US011976299B2

(12) United States Patent
Cafri et al.

(10) Patent No.: US 11,976,299 B2
(45) Date of Patent: May 7, 2024

(54) METHODS OF PREPARING AN ISOLATED POPULATION OF DENDRITIC CELLS AND METHODS OF TREATING CANCER USING SAME

(71) Applicant: The United States of America, as represented by the Secretary, Department of Health and Human Services, Bethesda, MD (US)

(72) Inventors: Gal Cafri, Rockville, MD (US); Paul F. Robbins, Chevy Chase, MD (US); Jared J. Gartner, Gaithersburg, MD (US); Steven A. Rosenberg, Potomac, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 543 days.

(21) Appl. No.: 16/334,872

(22) PCT Filed: Sep. 18, 2017

(86) PCT No.: PCT/US2017/051981
§ 371 (c)(1),
(2) Date: Mar. 20, 2019

(87) PCT Pub. No.: WO2018/057447
PCT Pub. Date: Mar. 29, 2018

(65) Prior Publication Data
US 2020/0017831 A1    Jan. 16, 2020

Related U.S. Application Data

(60) Provisional application No. 62/398,963, filed on Sep. 23, 2016.

(51) Int. Cl.
*A61K 35/15* (2015.01)
*C12N 5/0784* (2010.01)

(52) U.S. Cl.
CPC ............ *C12N 5/0639* (2013.01); *A61K 35/15* (2013.01); *C12N 2501/02* (2013.01); *C12N 2501/052* (2013.01); *C12N 2501/22* (2013.01); *C12N 2501/2301* (2013.01); *C12N 2501/2304* (2013.01); *C12N 2501/2306* (2013.01); *C12N 2501/24* (2013.01); *C12N 2501/25* (2013.01); *C12N 2501/52* (2013.01); *C12N 2501/999* (2013.01); *C12N 2502/1114* (2013.01)

(58) Field of Classification Search
CPC ................................ A61K 35/15; A61K 35/17
See application file for complete search history.

(56) References Cited

U.S. PATENT DOCUMENTS

| 7,820,174 | B2 | 10/2010 | Wang et al. | |
| 8,216,565 | B2 | 7/2012 | Restifo et al. | |
| 8,465,743 | B2 | 7/2013 | Rosenberg et al. | |
| 8,785,601 | B2 | 7/2014 | Rosenberg et al. | |
| 9,567,567 | B2 * | 2/2017 | Kirkin | C12N 5/0638 |
| 2006/0194318 | A1 * | 8/2006 | Shankar | A61K 39/12 |
|  |  |  |  | 435/372 |
| 2011/0293637 | A1 | 12/2011 | Hacohen et al. | |
| 2012/0328662 | A1 * | 12/2012 | Karlsson-Parra | A61P 35/00 |
|  |  |  |  | 424/278.1 |
| 2013/0274203 | A1 | 10/2013 | Morgan et al. | |
| 2014/0037628 | A1 | 2/2014 | Morgan et al. | |
| 2014/0274909 | A1 | 9/2014 | Orentas et al. | |
| 2015/0071892 | A1 * | 3/2015 | Ginis | A61P 31/10 |
|  |  |  |  | 424/93.71 |
| 2016/0008447 | A1 * | 1/2016 | Hacohen | A61P 43/00 |
|  |  |  |  | 424/174.1 |
| 2017/0224797 | A1 * | 8/2017 | Popescu | A61K 9/127 |

FOREIGN PATENT DOCUMENTS

| WO | WO 03/020889 A2 | 3/2003 |
| WO | WO 2004/072262 A2 | 8/2004 |
| WO | WO 2011/098516 A1 | 8/2011 |
| WO | WO 2011/143656 A2 | 11/2011 |
| WO | WO 2016/040900 A1 | 3/2016 |
| WO | WO 2016/053339 A1 | 4/2016 |

OTHER PUBLICATIONS

Cannon et al., "Novel target antigens for dendritic cell-based immunotherapy against ovarian cancer," *Exp. Rev. Anticancer Ther.*, 2(1): 97-105 (2002).
Carreno et al., "A dendritic cell vaccine increases the breadth and diversity of melanoma neoantigen-specific T cells," *Science.*, 348: 803-808 (2015).
Carreno et al., Supplemental Materials for "A dendritic cell vaccine increases the breadth and diversity of melanoma neoantigen-specific T cells," *Science.*, 348: 803-808 (2015).
Cohen et al., "Isolation of neoantigen-specific T cells from tumor and peripheral lymphocytes," *J. Clin. Invest.*, 125(10): 3981-3991 (2015).
Gros et al., "PD-1 identifies the patient-specific CD8+ tumor-reactive repertoire infiltrating human tumors," *J. Clin. Invest.*, 124(5): 2246-2259 (2014).
Gros et al., "Prospective identification of neoantigen-specific lymphocytes in the peripheral blood of melanoma patients," *Nat. Med.*, 22(4):433-438 (2016).
International Bureau, International Search Report and Written Opinion in International Application No. PCT/US2017/051981, dated Dec. 15, 2017.

(Continued)

*Primary Examiner* — Daniel C Gamett
(74) *Attorney, Agent, or Firm* — Leydig, Voit & Mayer Ltd.

(57) ABSTRACT

Disclosed are methods of preparing an isolated population of dendritic cells, isolated populations of dendritic cells prepared by the methods, and pharmaceutical compositions comprising the isolated population of dendritic cells. Also disclosed are methods of treating or preventing cancer using the isolated population of dendritic cells or pharmaceutical compositions.

8 Claims, 17 Drawing Sheets

Specification includes a Sequence Listing.

(56) References Cited

OTHER PUBLICATIONS

Kreiter et al., "Mutant MHC class II epitopes drive therapeutic immune responses to cancer," *Nature*, 520(7549): 692-696 (2015).
Lu et al., "Efficient Identification of Mutated Cancer Antigens Recognized by T Cells Associated with Durable Tumor Regressions," *Clin. Cancer Res.*, 20(13): 3401-3410 (2014).
Prickett et al., "Durable Complete Response from Metastatic Melanoma after Transfer of Autologous T Cells Recognizing 10 Mutated Tumor Antigens," *Cancer Immunol. Res.*, 4(8): 669-678 (2016).
Robbins et al., "Mining Exomic Sequencing Data to Identify Mutated Antigens Recognized by Adoptively Transferred Tumor-reactive T cells," *Nat. Med.*, 19(6): 747-752 (2013).
Ronaghi et al., "A sequencing method based on real-time pyrophosphate," *Science*, 281(5375): 363-365 (1998).
Steinman, "Decisions about dendritic cells: past, present, and future," *Annu. Rev. Immunol.*, 30: 1-22 (2012).
Tran et al., "Cancer Immunotherapy Based on Mutation-Specific CD4+ T Cells in a Patient with Epithelial Cancer," *Science*, 344: 641-645 (2014).
Tran et al., "Immunogenicity of somatic mutations in human gastrointestinal cancers," *Science*, 350(6266): 1387-1390 (2015).
Trolle et al., "Automated benchmarking of peptide-MHC class I binding predictions," *Bioinformatics*, 31(13): 2174-2181 (2015).
Turcotte et al., "Tumor-reactive CD8+ T cells in metastatic gastrointestinal cancer refractory to chemotherapy," *Clin. Cancer Res.*, 20(2): 331-343 (2013).
Voelkerding et al., "Next-generation sequencing: from basic research to diagnostics," *Clinical Chemistry*, 55: 641-658 (2009).
Zhang et al., "The impact of next-generation sequencing on genomics," *J. Genet. Genomics*, 38(3): 95-109 (2011).

\* cited by examiner

Basic TMG backbone

5' eERS2 NY-ESO HIST2H2BC ppp1R3B FDPS QSOX1 gp100 KIAA1804 HEY1 MAGEA3 KLHL21 FUBP1 HPV16E7 GTPBP4 SRP1 HPV16E6 PLCB3 Tyrosinase PPP2R5B ARHGEF2 - 3'

FIG. 4

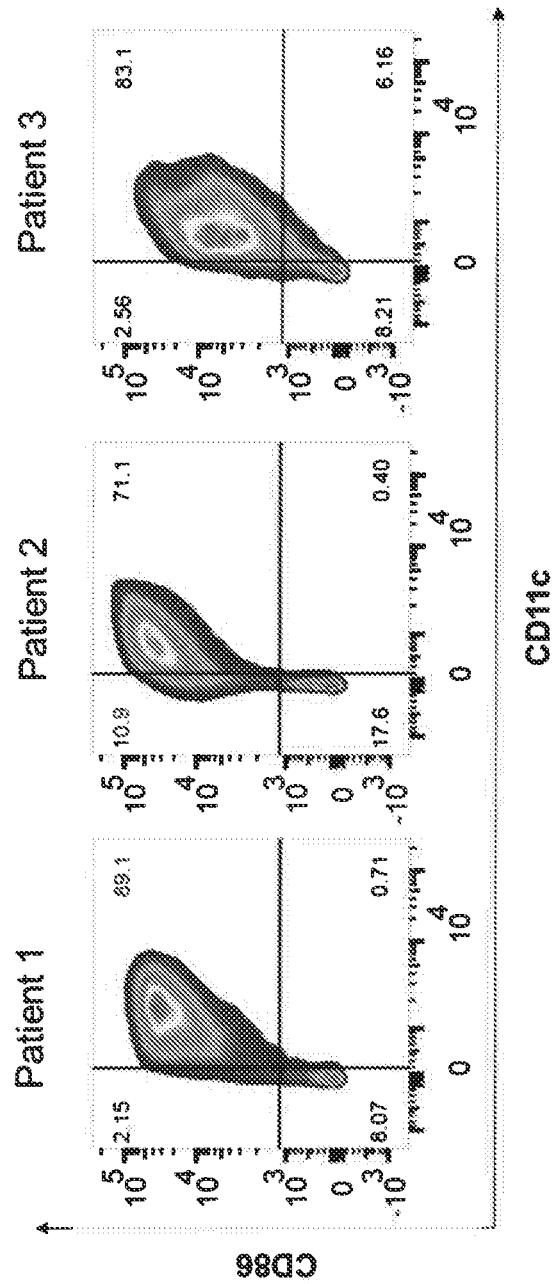

METHODS OF PREPARING AN ISOLATED POPULATION OF DENDRITIC CELLS AND METHODS OF TREATING CANCER USING SAME

CROSS-REFERENCE TO RELATED APPLICATIONS

This patent application is the U.S. national stage of PCT/US2017/051981, filed Sep. 18, 2017, which claims the benefit of U.S. Provisional Patent Application No. 62/398,963, filed Sep. 23, 2016, which is incorporated by reference in its entirety herein.

STATEMENT REGARDING FEDERALLY SPONSORED RESEARCH AND DEVELOPMENT

This invention was made with Government support under project number Z1ABC 010984 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 3,572 Byte ASCII (Text) file named "742109 ST25.TXT," dated Mar. 14, 2019.

BACKGROUND OF THE INVENTION

Protective vaccination against some infectious diseases has been an effective health measure. However, obstacles to the successful use of therapeutic vaccines against established diseases, such as cancer, remain. For example, T cells prompted using vaccines may undergo depletion of high avidity clones directed against target antigens. This depletion may cause the loss of T cells bearing high-affinity T cell receptors (TCRs) for their cognate antigens which have any one or more of superior cytotoxic capacity, longer persistence in the tumor microenvironment, and decreased susceptibility to immune suppression. Taking together, such depletion can impair clinical efficiency of the vaccine.

Accordingly, there is a need for improved methods of preparing compositions which may be useful for the treatment or prevention of cancer.

BRIEF SUMMARY OF THE INVENTION

An embodiment of the invention provides a method of preparing an isolated population of dendritic cells, the method comprising identifying one or more mutated amino acid sequences, each mutated amino acid sequence being encoded by a gene comprising a cancer-specific mutation; inducing first dendritic cells from a patient to present the one or more mutated amino acid sequences; co-culturing T cells from the patient with the first dendritic cells; selecting the one or more mutated amino acid sequences for which the T cells have antigenic specificity; isolating monocytes from the patient; differentiating the monocytes into second dendritic cells; inducing the second dendritic cells to present the selected one or more mutated amino acid sequences for which the T cells have antigenic specificity; and maturing the second dendritic cells to provide an isolated population of dendritic cells comprising the matured second dendritic cells which present the selected one or more mutated amino acid sequences for which the T cells have antigenic specificity.

Further embodiments of the invention provide an isolated population of dendritic cells prepared according to the inventive method and pharmaceutical compositions comprising the same.

Still another embodiment of the invention provides a method of treating or preventing cancer in a patient, the method comprising administering to the patient the inventive isolated population of dendritic cells or the inventive pharmaceutical composition in an amount effective to treat or prevent cancer in the patient.

BRIEF DESCRIPTION OF THE SEVERAL VIEWS OF THE DRAWING(S)

FIG. 4 is a schematic illustrating an example of a tandem minigene (TMG) backbone.

Figure 5A:
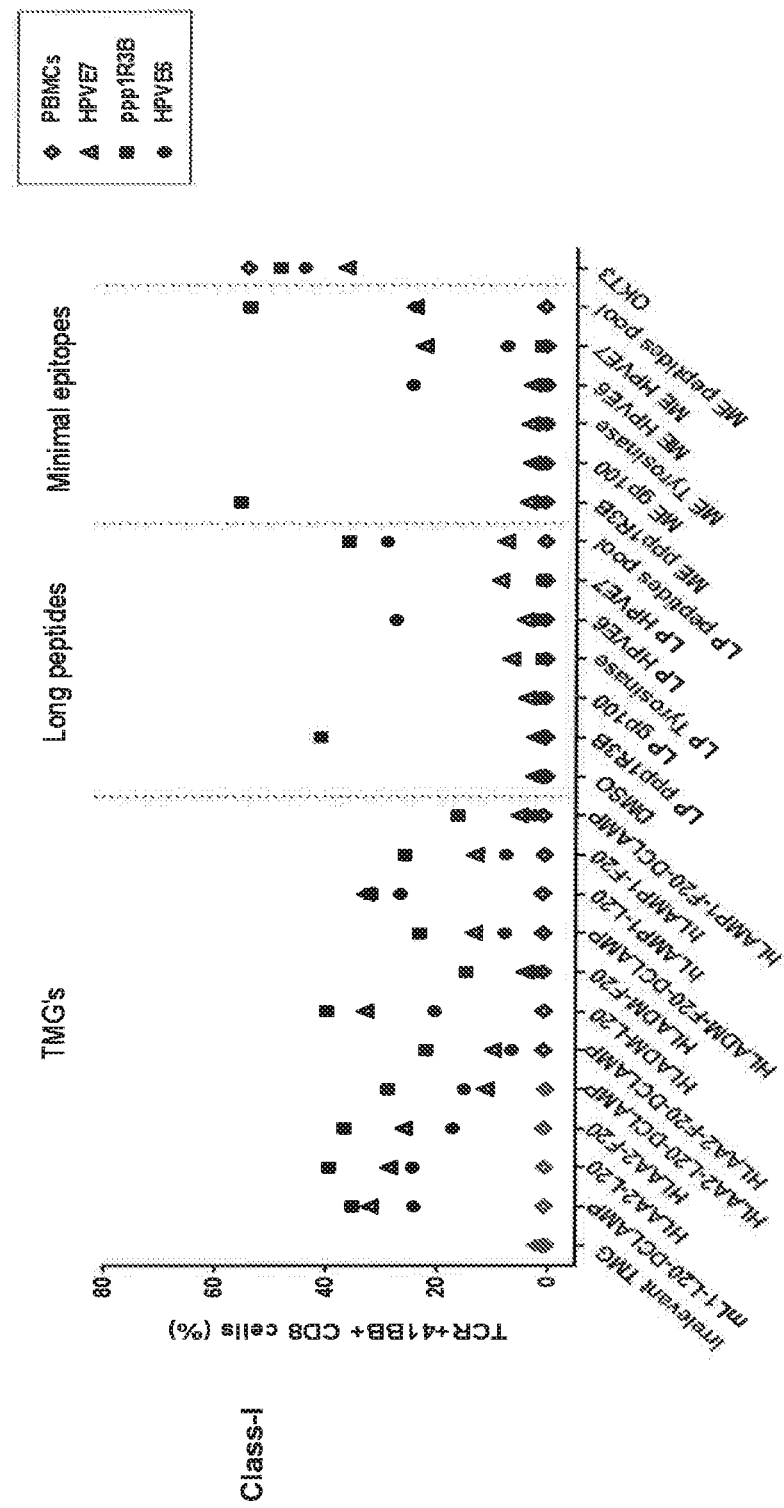

FIG. 5A is a graph showing the percentage of TCR+4-1BB+CD8+ effector cells detected following co-culture of DCs transfected with the indicated Class-I TMG construct, loaded with the indicated Class-I long peptide, or loaded with the indicated Class-I minimal epitope with effector cells. The effector cells were PBMC (diamonds) or cells transduced with a TCR having antigenic specificity for Class I peptides of HPV E7 (triangles), HPV E6 (circles), or ppp1R3B (squares).

Figure 5B:
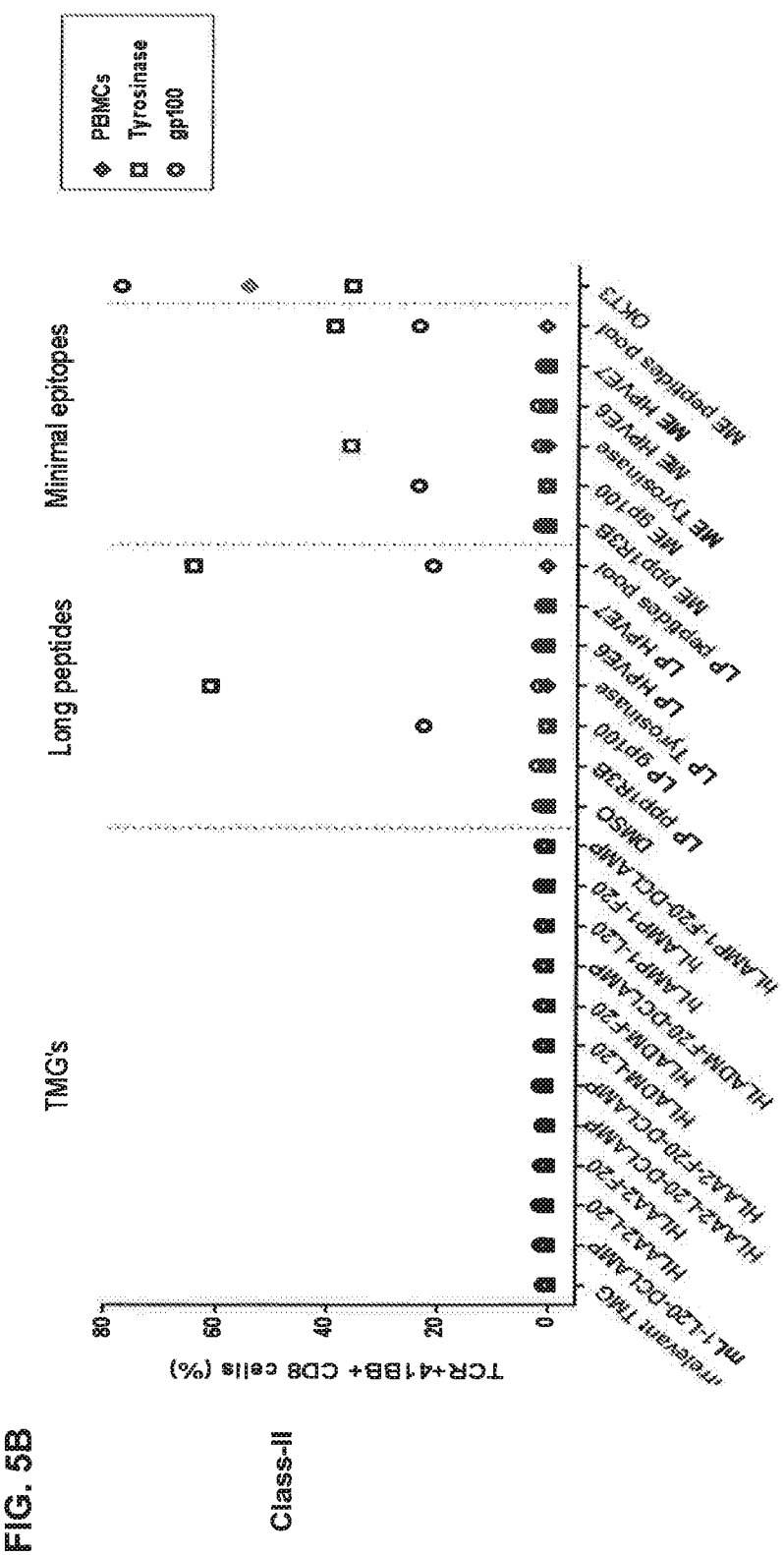

FIG. 5B is a graph showing the percentage of TCR+4-1BB+CD8+ effector cells detected following co-culture of DCs transfected with the indicated Class-II TMG construct, loaded with the indicated Class-II long peptide, or loaded with the indicated Class-II minimal epitope with effector cells. The effector cells were PBMC (diamonds) or cells transduced with a TCR having antigenic specificity for Class II peptides of gp100 E6 (circles) or tyrosinase (squares).

Figure 6A:
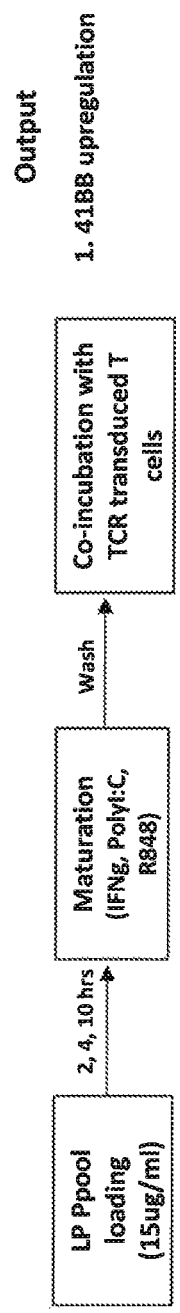

FIG. 6A is a schematic illustrating a method comprising loading DCs with long peptides (LP), maturing the DCs, and co-incubating the matured DCs with TCR-transduced T cells.

Figure 6B:
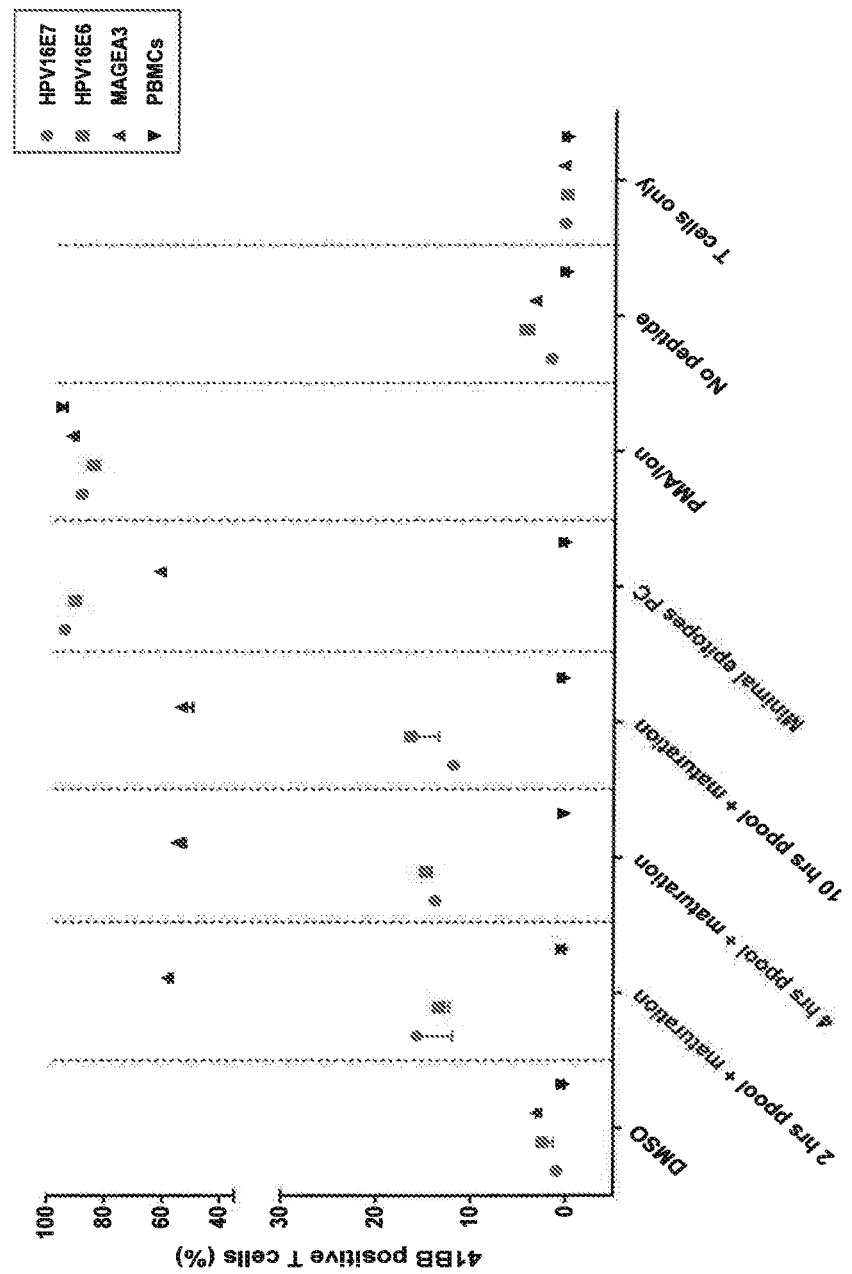

FIG. 6B is a graph showing the percentage of 4-1BB positive T cells measured following co-culture of PBMCs which were untransduced (PBMCs; ▼) or transduced with a TCR having antigenic specificity for HPV 16 E7 (circles), HPV 16 E6 (squares), MAGE A3 (▲) with DCs which were treated with (i) DMSO, (ii) phorbol 12-myristate 13-acetate (PMA) and ionomycin (Ion), or (iii) no peptide; (iv) loaded with a peptide pool for 2, 4, or 10 hours and matured for 16 hours using the TLR mix; or (v) loaded with minimal epitopes (positive control). T cells cultured alone served as a control.

Figure 7:
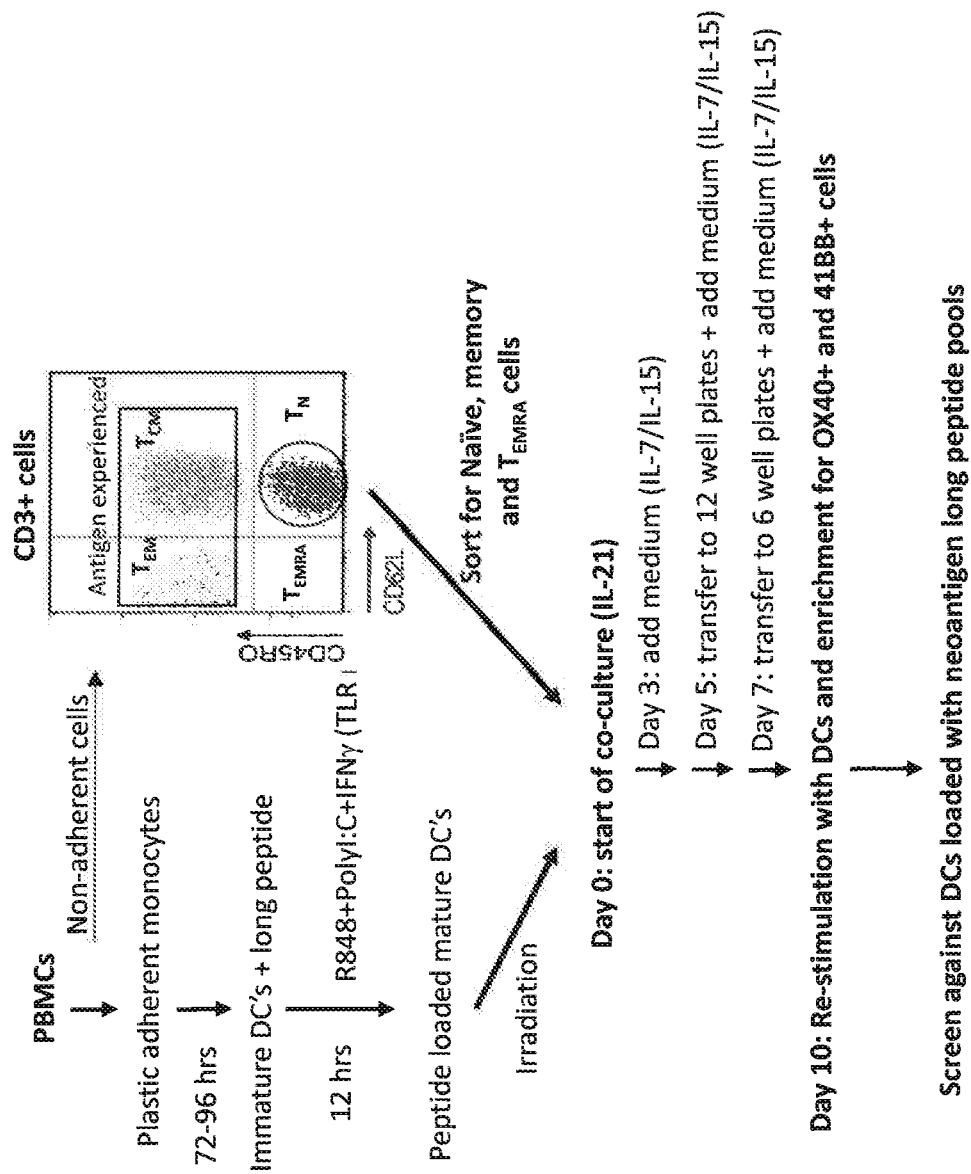
Figure 8A:
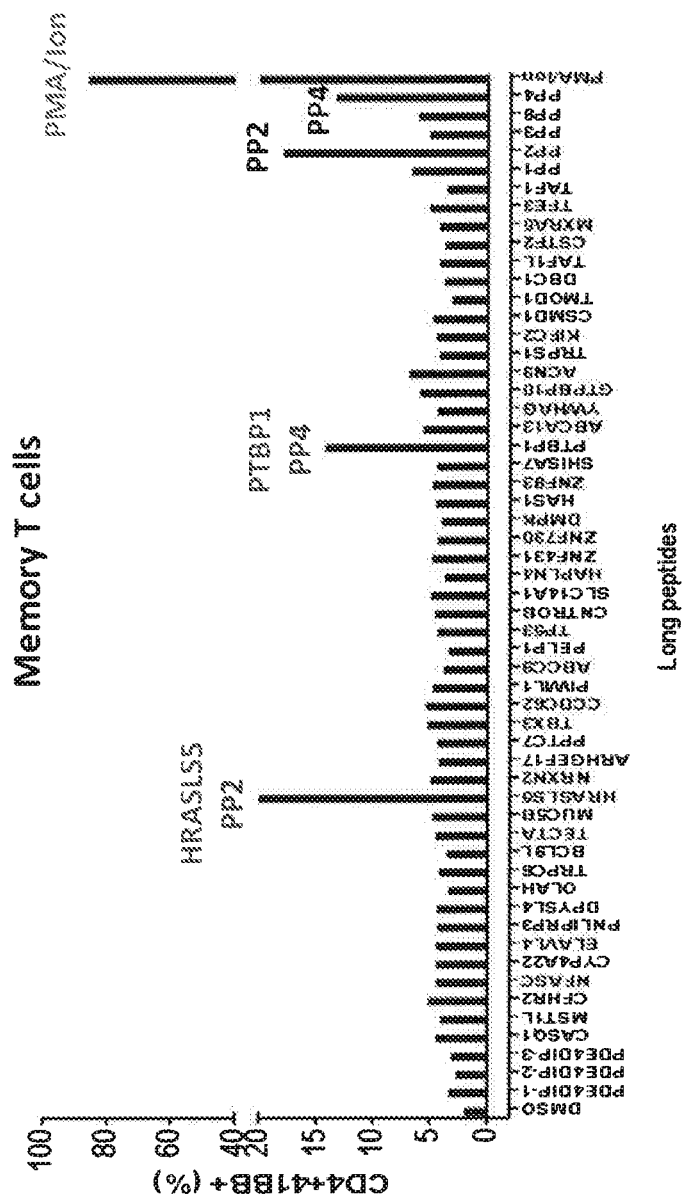
Figure 8B:
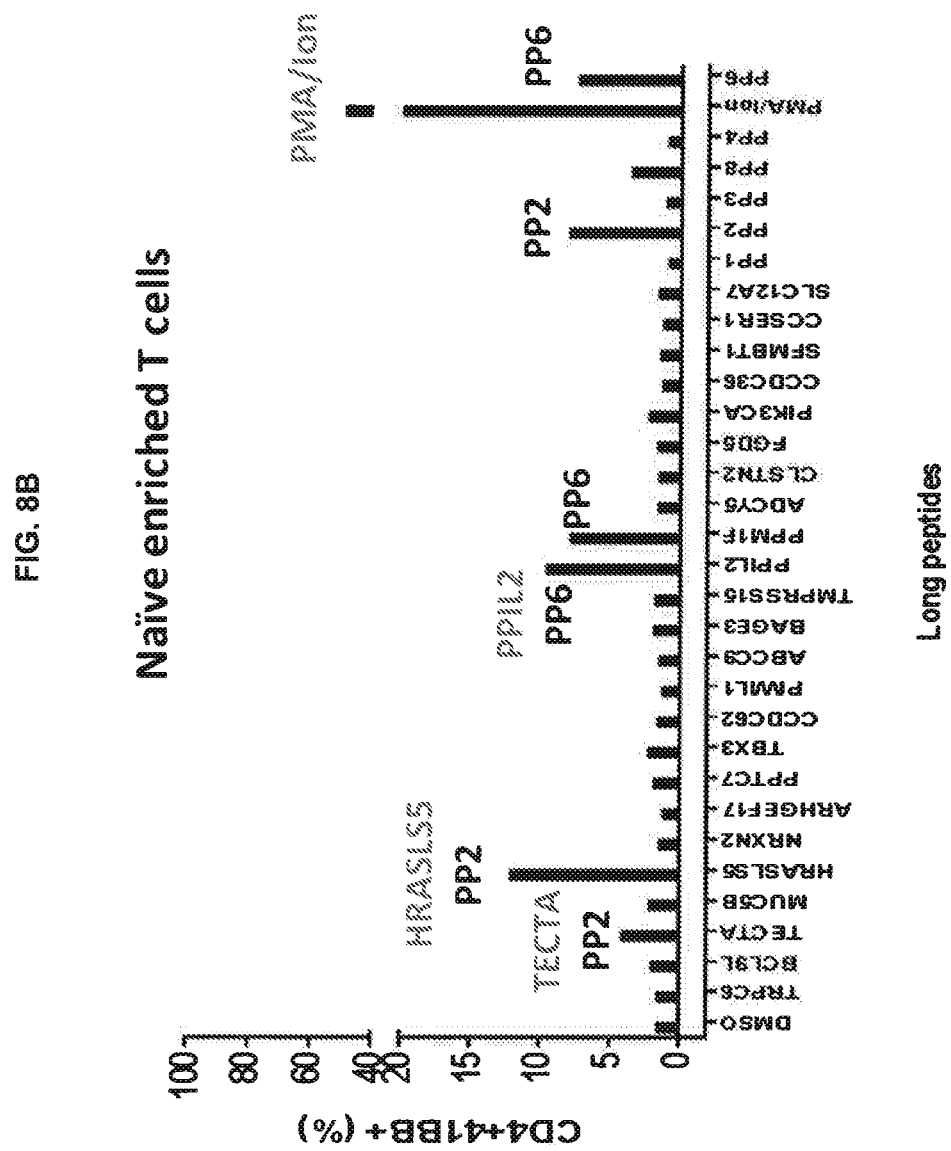
Figure 8C:
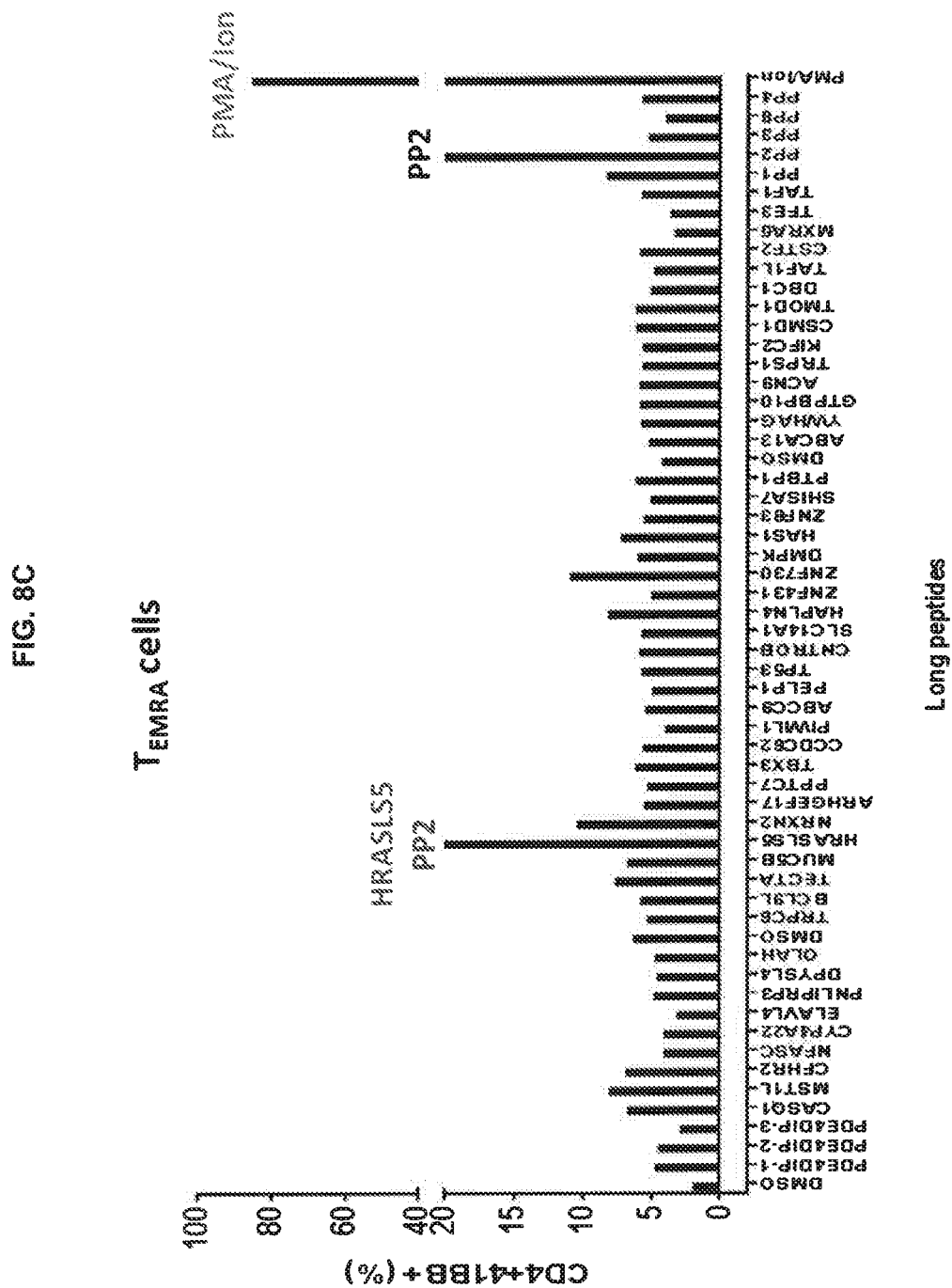
Figure 8D:
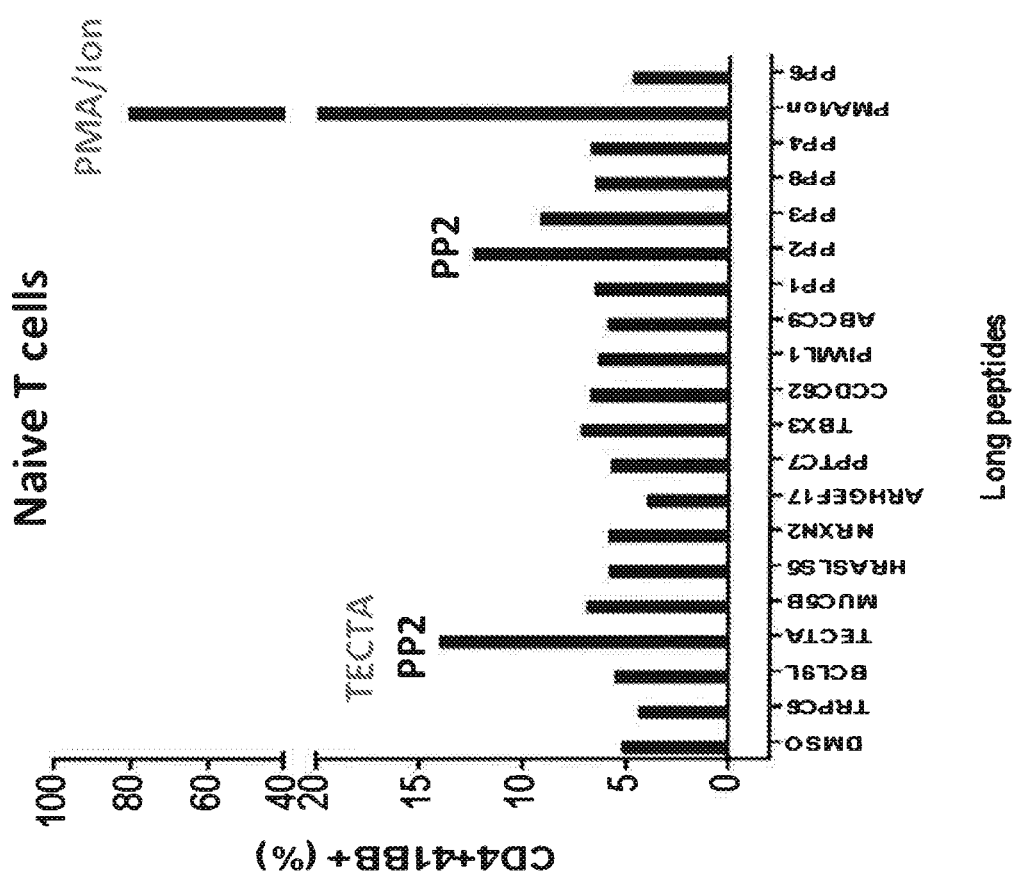

FIG. 7 is a schematic illustrating a method of evaluating the activation of neoantigen-specific T cells.

FIGS. 8A-8D are graphs showing the percentage of CD4+4-1BB+ memory T cells (A), naïve enriched T cells (B), $T_{EMRA}$ cells (C), or naïve T cells (D) obtained following co-culture with DCs matured with TLR mix and loaded with the indicated long peptide.

Figure 9B:
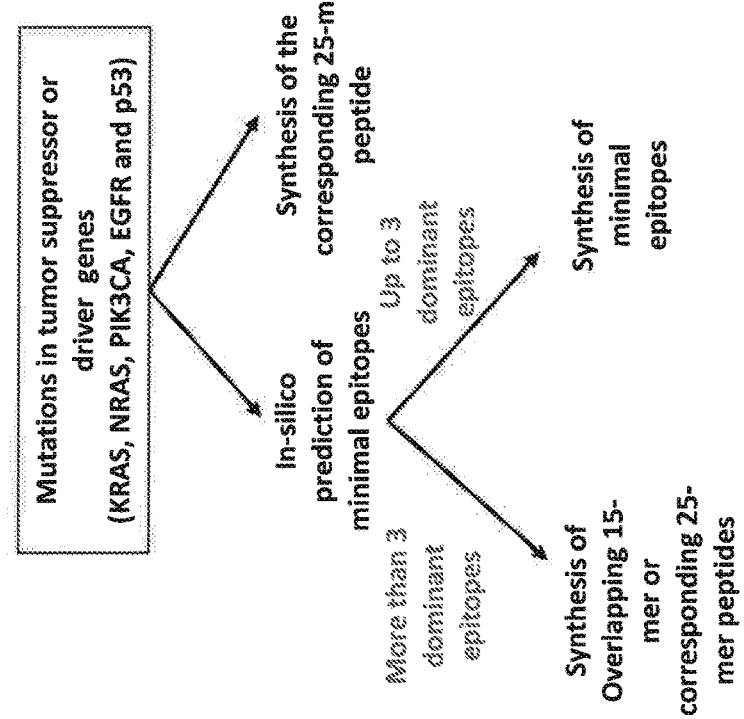
Figure 9A:
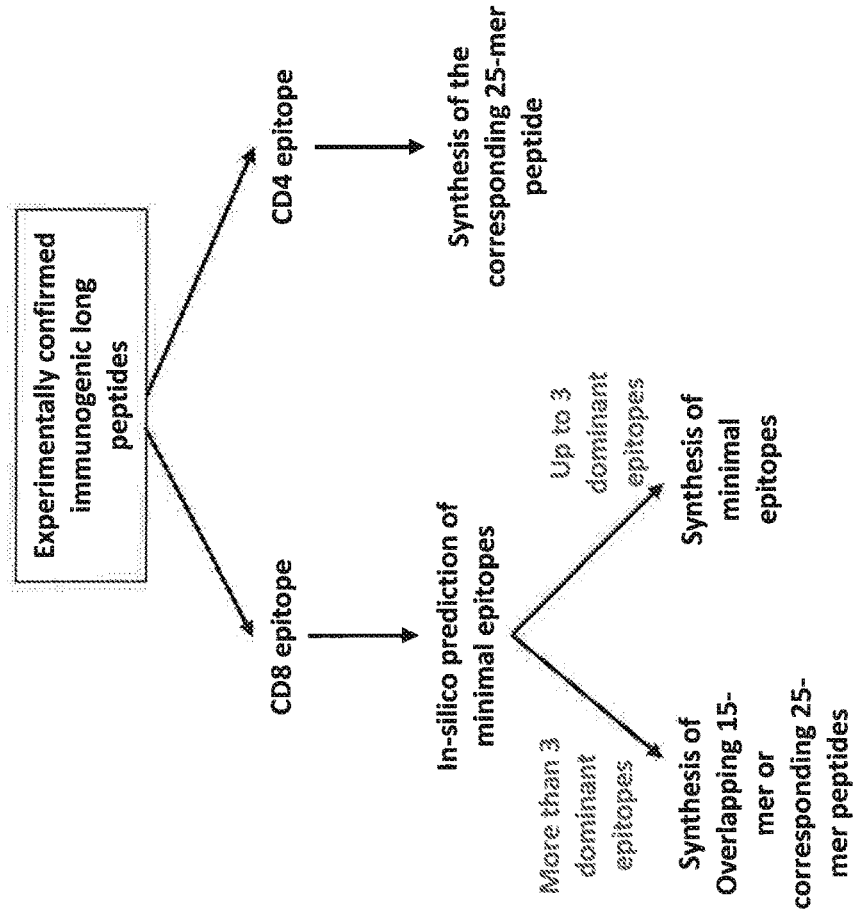

FIGS. 9A and 9B are schematics illustrating a method of selecting and synthesizing epitopes.

Figures 11A, 11B:
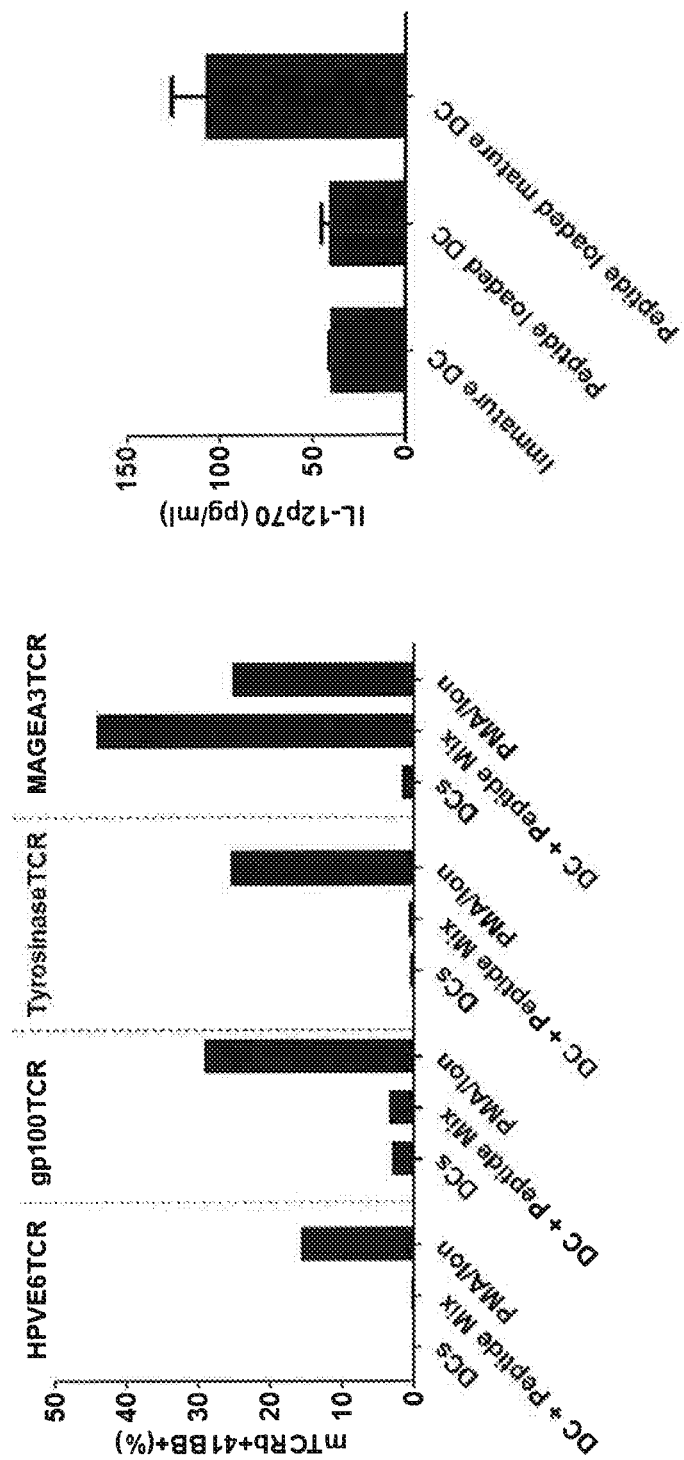

FIG. 10 shows flow cytometry dot plots illustrating the expression of CD86 and CD11c by DC from Patients 1, 2, and 3 which were prepared as described in Example 6. The numbers in the dot plots represent the percentages of CD86+/CD11c+ (upper right corner), CD86+/CD11c− (upper left corner), CD86−/CD11c+(lower right corner), and CD86−/CD11c− (lower left corner) cells. FIG. 11A is a graph showing the percentage of PBMC transduced with an anti-HPV E6, anti-gp100, anti-tyrosinase, or anti-MAGE-A3 mTCR (mTCR beta chain positive cells) expressing 4-1BB following co-culture with DCs alone, DCs with a mix of the corresponding peptide, or phorbol myristate acetate (PMA) and ionomycin.

FIG. 11B is a graph showing the amount of IL-12p70 (pg/ml) secreted by DCs (i) before peptide loading (immature DC), (ii) after peptide loading and before maturation (peptide loaded DC), and (iii) after maturation and peptide loading (peptide loaded mature DC).

DETAILED DESCRIPTION OF THE INVENTION

An embodiment of the invention provides a method of preparing an isolated population of dendritic cells. The isolated population of dendritic cells may be included in a pharmaceutical composition useful for the treatment or prevention of cancer (e.g., as a cancer vaccine).

The invention may provide many advantages. For example, the inventive methods may rapidly assess a large number of mutations restricted by all of the patient's MHC molecules at one time, which may identify the full repertoire of cancer-specific mutations recognized by the patient's T cells. The cancer-specific mutations identified by the inventive methods may include neoantigens derived from somatic mutations. Without being bound to a particular theory or mechanism, it is believed that neoantigens derived from somatic mutations may reduce or avoid the disadvantages associated with central immunological tolerance to any one or more of differentiation antigens, cancer testis antigens, and overexpressed antigens. The targeting of neoantigens may reduce or avoid, for example, one or both of the depletion of high avidity clones directed against the antigen and the loss of T cells bearing high-affinity TCRs for their cognate antigens. Alternatively or additionally, the targeting of neoantigens may provide any one or more of increased cytotoxic capacity, increased persistence in the tumor microenvironment, and decreased susceptibility to immune suppression, particularly as compared to the targeting of any one or more of differentiation antigens, cancer testis antigens, and overexpressed antigens. Accordingly, it is believed that the inventive methods may provide a pharmaceutical composition (e.g., vaccine) that has improved clinical efficacy as compared to pharmaceutical compositions which target any one or more of differentiation antigens, cancer testis antigens, and overexpressed antigens.

Additionally, by distinguishing immunogenic cancer mutations from (a) silent cancer-specific mutations (which do not encode a mutated amino acid sequence) and (b) cancer-specific mutations that encode a non-immunogenic amino acid sequence, the inventive methods may identify one or more cancer-specific, mutated amino acid sequences that may be targeted by a T cell. In addition, the invention may provide dendritic cells which present one or more mutated amino acid sequences encoded by cancer-specific mutations that are unique to the patient, thereby providing an isolated, "personalized" population of dendritic cells that may be useful for preparing cells for adoptive cell therapies, e.g., for treating or preventing the patient's cancer. The inventive methods may also avoid the technical biases inherent in traditional methods of identifying cancer antigens such as, for example, those using cDNA libraries, and may also be less time-consuming and laborious than those methods. Without being bound to a particular theory or mechanism, it is believed that the inventive methods may target the destruction of cancer cells while minimizing or eliminating the destruction of normal, non-cancerous cells, thereby reducing or eliminating toxicity. Accordingly, the invention may also provide dendritic cells that successfully treat or prevent cancer such as, for example, cancers that do not respond to other types of treatment such as, for example, chemotherapy alone, surgery, or radiation.

The method of preparing an isolated population of dendritic cells may comprise identifying one or more mutated amino acid sequences, each mutated amino acid sequence being encoded by a gene in the nucleic acid of a cancer cell of a patient, wherein the gene comprises a cancer-specific mutation. The cancer cell may be obtained from any bodily sample derived from a patient which contains or is expected to contain tumor or cancer cells. The bodily sample may be any tissue sample such as blood, a tissue sample obtained from the primary tumor or from tumor metastases, or any other sample containing tumor or cancer cells. The nucleic acid of the cancer cell may be DNA or RNA.

In order to identify one or more mutated amino acid sequences each encoded by a gene comprising a cancer-specific mutation, the method may further comprise sequencing nucleic acid such as DNA or RNA of normal, noncancerous cells and comparing the sequence of the cancer cell with the sequence of the normal, noncancerous cell. The normal, noncancerous cell may be obtained from the patient or a different individual.

The cancer-specific mutation may be any mutation in any gene which encodes a mutated amino acid sequence (also referred to as a "non-silent mutation") and which is expressed in a cancer cell but not in a normal, noncancerous cell. Non-limiting examples of cancer-specific mutations that may encode mutated amino acid sequences identified in the inventive methods include missense, nonsense, insertion, deletion, duplication, frameshift, and repeat expansion mutations. In an embodiment of the invention, the method comprises identifying at least one mutated amino acid sequence encoded by a gene containing a cancer-specific mutation. However, the number of mutated amino acid sequences that may be identified using the inventive methods is not limited and may include more than one mutated amino acid sequence (for example, about 2, about 3, about 4, about 5, about 10, about 11, about 12, about 13, about 14, about 15, about 20, about 25, about 30, about 40, about 50, about 60, about 70, about 80, about 90, about 100, about 150, about 200, about 400, about 600, about 800, about 1000, about 1500, about 2000 or more, or a range defined by any two of the foregoing values). Likewise, in an embodiment of the invention, the method comprises identifying at least one mutated amino acid sequence encoded by a gene comprising a cancer-specific mutation. However, the number of such mutated amino acid sequences that may be identified using the inventive methods is not limited and may include more than one mutated amino acid sequence (for example, about 2, about 3, about 4, about 5, about 10, about 11, about 12, about 13, about 14, about 15, about 20, about 25, about 30, about 40, about 50, about 60, about 70, about 80, about 90, about 100, about 150, about 200, about 400, about 600, about 800, about 1000, about 1500, about 2000 or more, or a range defined by any two of the foregoing values). In an embodiment in which more than one mutated amino acid sequence is identified, the mutated amino acid sequences may be encoded by the same mutated gene or by different mutated genes.

In an embodiment, the method comprises sequencing the whole exome, the whole genome, or the whole transcriptome of the cancer cell. Sequencing may be carried out in any suitable manner known in the art. Examples of sequencing techniques that may be useful in the inventive methods include Next Generation Sequencing (NGS) (also referred to as "massively parallel sequencing technology") or Third Generation Sequencing. NGS refers to non-Sanger-based high-throughput DNA sequencing technologies. With NGS, millions or billions of DNA strands may be sequenced in parallel, yielding substantially more throughput and minimizing the need for the fragment-cloning methods that are often used in Sanger sequencing of genomes. In NGS, nucleic acid templates may be randomly read in parallel along the entire genome by breaking the entire genome into small pieces. NGS may, advantageously, provide nucleic acid sequence information of a whole genome, exome, or transcriptome in very short time periods, e.g., within about 1 to about 2 weeks, preferably within about 1 to about 7 days, or most preferably, within less than about 24 hours. Multiple NGS platforms which are commercially available or which are described in the literature can be used in the context of the inventive methods, e.g., those described in Zhang et al., *J. Genet. Genomics*, 38(3): 95-109 (2011) and Voelkerding et al., *Clinical Chemistry*, 55: 641-658 (2009).

Non-limiting examples of NGS technologies and platforms include sequencing-by-synthesis (also known as "pyrosequencing") (as implemented, e.g., using the GS-FLX 454 Genome Sequencer, 454 Life Sciences (Branford, CT), ILLUMINA SOLEXA Genome Analyzer (Illumina Inc., San Diego, CA), or the ILLUMINA HISEQ 2000 Genome Analyzer (Illumina), or as described in, e.g., Ronaghi et al., Science, 281(5375): 363-365 (1998)), sequencing-by-ligation (as implemented, e.g., using the SOLID platform (Life Technologies Corporation, Carlsbad, CA) or the POLONATOR G.007 platform (Dover Systems, Salem, NH)), single-molecule sequencing (as implemented, e.g., using the PACBIO RS system (Pacific Biosciences (Menlo Park, CA) or the HELISCOPE platform (Helicos Biosciences (Cambridge, MA)), nano-technology for single-molecule sequencing (as implemented, e.g., using the GRIDON platform of Oxford Nanopore Technologies (Oxford, UK), the hybridization-assisted nano-pore sequencing (HANS) platforms developed by Nabsys (Providence, RI), and the ligase-based DNA sequencing platform with DNA nanoball (DNB) technology referred to as probe-anchor ligation (cPAL)), electron microscopy-based technology for single-molecule sequencing, and ion semiconductor sequencing.

The method may comprise inducing first dendritic cells from the patient to present the one or more mutated amino acid sequences. In this regard, the first dendritic cells may be autologous to the patient. The first dendritic cells may present peptide fragments comprising the one or more mutated amino acid sequences in association with major histocompatibility complex (MHC) molecules on their cell surface. By using autologous dendritic cells from the patient, the inventive methods may, advantageously, identify one or more mutated amino acid sequences that are recognized by the patient's T cells when the one or more mutated amino acid sequences are presented in the context of an MHC molecule expressed by the patient. The MHC molecule can be any MHC molecule expressed by the patient including, but not limited to, MHC Class I, MHC Class II, HLA-A, HLA-B, HLA-C, HLA-DM, HLA-DO, HLA-DP, HLA-DQ, and HLA-DR molecules. Accordingly, in an embodiment of the invention, the inventive methods advantageously identify mutated amino acid sequences presented in the context of any MHC molecule expressed by the patient and are not limited to any particular MHC molecule. Preferably, the first dendritic cells are antigen-negative dendritic cells.

Inducing first dendritic cells from the patient to present the one or more mutated amino acid sequences may be carried out using any suitable method known in the art. In an embodiment of the invention, inducing the first dendritic cells to present the one or more mutated amino acid sequences comprises pulsing the first dendritic cells with peptides comprising the mutated amino acid sequence or a pool of peptides, each peptide in the pool comprising a different mutated amino acid sequence. Each of the mutated amino acid sequences in the pool may be encoded by a gene containing a cancer specific mutation. In this regard, the first dendritic cells may be cultured with a peptide or a pool of peptides comprising the one or more mutated amino acid sequences in a manner such that the dendritic cells internalize the peptide(s) and display the mutated amino acid sequence(s), bound to an MHC molecule, on the cell membrane. In an embodiment in which more than one mutated amino acid sequence is identified, each mutated amino acid sequence being encoded by a gene comprising a cancer-specific mutation, the method may comprise pulsing the first dendritic cells with a pool of peptides, each peptide in the pool comprising a different mutated amino acid sequence. Methods of pulsing dendritic cells are known in the art and are described in, e.g., Solheim (Ed.), *Antigen Processing and Presentation Protocols (Methods in Molecular Biology)*, Human Press, (2010). The peptide(s) used to pulse the first dendritic cells may include the mutated amino acid(s) encoded by the cancer-specific mutation. The peptide(s) may further comprise any suitable number of contiguous amino acids from the endogenous protein encoded by the gene on each of the carboxyl side and the amino side of the mutated amino acid(s). The number of contiguous amino acids from the endogenous protein flanking each side of the mutation is not limited and may be, for example, about 4, about 5, about 6, about 7, about 8, about 9, about 10, about 11, about 12, about 13, about 14, about 15, about 16, about 17, about 18, about 19, about 20, or a range defined by any two of the foregoing values. Preferably, the peptide(s) comprise(s) about 12 contiguous amino acids from the endogenous protein on each side of the mutated amino acid(s). Accordingly, in an embodiment of the invention, the peptide(s) may have a length of about 15 to about 40 amino acid residues or about 20 to about 30 amino acid residues, preferably about 25 amino acid residues. In an embodiment of the invention, the peptide(s) may comprise a minimal T cell epitope comprising the mutated amino acid sequence. In this regard, the peptide(s) may have a shorter length, e.g., a length of about 8 to about 19 amino acid residues. The minimal T cell epitope may be determined by prediction in silico as described, for example, in Trolle et al., *Bioinformatics*, 31(13): 2174-81 (2015) or through experimentation. In an embodiment of the invention, the method further comprises predicting in silico one or more minimal epitopes for which the T cells have antigenic specificity, wherein the peptides comprise the one or predicted minimal epitopes.

In an embodiment of the invention, inducing the first dendritic cells from the patient to present the one or more mutated amino acid sequence(s) comprises introducing nucleotide sequence(s) encoding the one or more mutated amino acid sequence into the first dendritic cells. The nucleotide sequence(s) is/are introduced into the dendritic cells so that the dendritic cells express and display the one or more mutated amino acid sequences, bound to an MHC molecule, on the cell membrane. The nucleotide sequence(s) encoding the mutated amino acid may be RNA or DNA. Introducing nucleotide sequence(s) into dendritic cells may be carried out in any of a variety of different ways known in the art as described in, e.g., Solheim et al. supra. Non-limiting examples of techniques that are useful for introducing nucleotide sequence(s) into dendritic cells include transformation, transduction, transfection, and electroporation. In an embodiment in which more than one mutated amino acid sequence is identified, the method may comprise preparing more than one nucleotide sequence, each encoding a mutated amino acid sequence encoded by a different gene, and introducing each nucleotide sequence into a different population of dendritic cells. In this regard, multiple populations of dendritic cells, each population expressing and displaying a different mutated amino acid sequence, may be obtained.

In an embodiment in which more than one mutated amino acid sequence is identified, each mutated amino acid sequence being encoded by a gene comprising a cancer-specific mutation, the method may comprise introducing a nucleotide sequence encoding more than one gene, each gene having a cancer-specific mutation. In this regard, in an embodiment of the invention, the nucleotide sequence introduced into the first dendritic cells is a tandem minigene (TMG) construct, each minigene comprising a different gene, each gene including a cancer-specific mutation that encodes a mutated amino acid sequence. Each minigene may encode one mutation identified by the inventive methods flanked on each side of the mutation by any suitable number of contiguous amino acids from the endogenous protein encoded by the gene, as described herein with respect to other aspects of the invention. The number of minigenes in the construct is not limited and may include for example, about 5, about 10, about 11, about 12, about 13, about 14, about 15, about 20, about 25, or more, or a range defined by any two of the foregoing values. The dendritic cells express the mutated amino acid sequences encoded by the TMG construct and display the mutated amino acid sequences, bound to an MHC molecule, on the cell membranes. In an embodiment, the method may comprise preparing more than one TMG construct, each construct encoding a different set of mutated amino acid sequences encoded by different genes, and introducing each TMG construct into a different population of dendritic cells. In this regard, multiple populations of dendritic cells, each population expressing and displaying mutated amino acid sequences encoded by different TMG constructs, may be obtained.

The method may comprise culturing T cells from the patient with the first dendritic cells that present the one or more mutated amino acid sequences. Preferably, the T cells are autologous to the patient. The T cells can be obtained from numerous sources in the patient, including but not limited to tumor, blood, bone marrow, lymph node, the thymus, or other tissues or fluids. The T cells can include any type of T cell and can be of any developmental stage, including but not limited to, CD4+/CD8+ double positive T cells, CD4+ helper T cells, e.g., Th1 and Th2 cells, CD8+ T cells (e.g., cytotoxic T cells), tumor infiltrating cells (e.g., tumor infiltrating lymphocytes (TIL)), peripheral blood T cells, memory T cells, naïve T cells, and the like. The T cells may be CD8+ T cells, CD4+ T cells, or both CD4+ and CD8+ T cells. The method may comprise co-culturing the T cells and the first dendritic cells so that the T cells encounter the one or more mutated amino acid sequence(s) presented by the first dendritic cells in such a manner that the T cells specifically bind to and immunologically recognize one or more mutated amino acid sequence(s) presented by the first dendritic cells. In an embodiment of the invention, the T cells are co-cultured in direct contact with the first dendritic cells.

The method may further comprise selecting the one or more mutated amino acid sequences for which the T cells have antigenic specificity. The phrase "antigenic specificity," as used herein, means that the T cells can specifically bind to and immunologically recognize the mutated amino acid sequence encoded by the cancer-specific mutation. The selecting may comprise identifying the one or more mutated amino acid sequences for which the T cells have antigenic specificity and separating them from the one or more mutated amino acid sequences for which the T cells do not have antigenic specificity. A single T cell from the patient will usually have antigenic specificity for no more than one mutated amino acid sequence. However, a plurality of T cells from the patient may comprise two or more T cells, each T cell having antigenic specificity for a different mutated amino acid sequence. Selecting the one or more mutated amino acid sequence for which the T cells have antigenic specificity may be carried out in any suitable manner.

For example, upon co-culture of the T cells with the first dendritic cells which present the one or more mutated amino acid sequences, T cells having antigenic specificity for the mutated amino acid sequence(s) may express any one or more of a variety of T cell activation markers which may be used to identify those mutated amino acid sequence(s) for which the T cells have antigenic specificity. Such T cell activation markers may include, but are not limited to, programmed cell death 1 (PD-1), lymphocyte-activation gene 3 (LAG-3), T cell immunoglobulin and mucin domain 3 (TIM-3), 4-1BB, OX40, and CD107a. Accordingly, in an embodiment of the invention, T cells which are co-cultured with the first dendritic cells which present the selected one or more mutated amino acid sequences may express any one or more of PD-1, LAG-3, TIM-3, 4-1BB, OX40, and CD107a. T cells expressing one or more T cell activation markers may be identified by sorting on the basis of expression of the marker using any of a variety of techniques known in the art such as, for example, fluorescence-activated cell sorting (FACS) or magnetic-activated cell sorting (MACS) as described in, e.g., Turcotte et al., *Clin. Cancer Res.*, 20(2): 331-43 (2013) and Gros et al., *J. Clin. Invest.*, 124(5): 2246-59 (2014).

In another embodiment of the invention, selecting the one or more mutated amino acid sequences for which the T cells have antigenic specificity comprises selecting those one or more mutated amino acid sequences which, upon presentation to the T cells, result in the T cells secreting one or more cytokines characteristic of T cell activation. For example, T cells having antigenic specificity for the mutated amino acid sequence may be characterized by T cells (i) that secrete a greater amount of one or more cytokines upon co-culture with dendritic cells that present the mutated amino acid sequence as compared to the amount of the one or more cytokines secreted by a negative control or (ii) in which at least twice as many of the numbers of T cells secrete one or more cytokines upon co-culture with dendritic cells that present the mutated amino acid sequence as compared to the numbers of negative control T cells that secrete the one or more cytokines. The one or more cytokines may comprise any cytokine the secretion of which by a T cell is characteristic of T cell activation (e.g., a T cell receptor (TCR) expressed by the T cells specifically binding to and immunologically recognizing the mutated amino acid sequence). Non-limiting examples of cytokines, the secretion of which is characteristic of T cell activation, include IFN-γ, IL-2, and tumor necrosis factor alpha (TNF-α), granulocyte/monocyte colony stimulating factor (GM-CSF), IL-4, IL-5, IL-9, IL-10, IL-17, and IL-22.

For example, T cells having antigenic specificity for the mutated amino acid sequence may be characterized by T cells that secrete at least twice as much IFN-γ upon co-culture with (a) antigen-negative dendritic cells pulsed with a concentration of a peptide comprising the mutated amino acid sequence (e.g., about 0.05 ng/mL to about 10 µg/mL, e.g., 0.05 ng/mL, 0.1 ng/mL, 0.5 ng/mL, 1 ng/mL, 5 ng/mL, 100 ng/mL, 1 µg/mL, 5 µg/mL, or 10 µg/mL) or (b) dendritic cells into which a nucleotide sequence encoding the mutated amino acid sequence has been introduced as compared to the amount of IFN-γ secreted by a negative control. The negative control may be, for example, autologous T cells (e.g., derived from peripheral blood mononuclear cells (PBMC)) co-cultured with (a) antigen-negative dendritic cells pulsed with the same concentration of an irrelevant peptide (e.g., the wild-type amino acid sequence, or some other peptide with a different sequence from the mutated amino acid sequence) or (b) dendritic cells into which a nucleotide sequence encoding an irrelevant peptide sequence has been introduced. The autologous T cells may also have "antigenic specificity" for the mutated amino acid sequence if the T cells secrete a greater amount of IFN-γ upon co-culture with antigen-negative dendritic cells pulsed with higher concentrations of a peptide comprising the mutated amino acid sequence as compared to a negative control, for example, the negative control described above. IFN-γ secretion may be measured by methods known in the art such as, for example, enzyme-linked immunosorbent assay (ELISA).

Alternatively or additionally, the T cells may be considered to have "antigenic specificity" for the mutated amino acid sequence if at least twice as many of the numbers of T cells secrete IFN-γ upon co-culture with (a) antigen-negative dendritic cells pulsed with a concentration of a peptide comprising the mutated amino acid sequence or (b) dendritic cells into which a nucleotide sequence encoding the mutated amino acid sequence has been introduced as compared to the numbers of negative control T cells that secrete IFN-γ. The concentration of peptide and the negative control may be as described herein with respect to other aspects of the invention. The numbers of cells secreting IFN-γ may be measured by methods known in the art such as, for example, ELISPOT.

While T cells having antigenic specificity for the mutated amino acid sequence may both (1) express any one or more T cells activation markers described herein and (2) secrete a greater amount of one or more cytokines as described herein, in an embodiment of the invention, T cells having antigenic specificity for the mutated amino acid sequence may express any one or more T cell activation markers without secreting a greater amount of one or more cytokines or may secrete a greater amount of one or more cytokines without expressing any one or more T cell activation markers.

In an embodiment of the invention in which T cells are co-cultured with dendritic cells expressing multiple mutated amino acid sequences (e.g., multiple mutated amino acid sequences encoded by a TMG construct or multiple mutated amino acid sequences in a pool of peptides pulsed onto dendritic cells), selecting the one or more mutated amino acid sequences for which the T cells have antigenic specificity may further comprise separately assessing T cells for antigenic specificity for each of the multiple mutated amino acid sequences. For example, the inventive method may further comprise separately inducing dendritic cells of the patient to present each mutated amino acid sequence encoded by the construct (or included in the pool), as described herein with respect to other aspects of the invention (for example, by providing separate dendritic cell populations, each presenting a different mutated amino acid sequence encoded by the construct (or included in the pool)). The method may further comprise separately co-culturing T cells of the patient with the different populations of dendritic cells that present each mutated amino acid sequence, as described herein with respect to other aspects of the invention. The method may further comprise separately selecting the one or more mutated amino acid sequences for which the T cells have antigenic specificity, as described herein with respect to other aspects of the invention. In this regard, the method may comprise determining which mutated amino acid sequence encoded by a TMG construct that encodes multiple mutated amino acid sequences (or included in the pool) are immunologically recognized by the T cells (e.g., by process of elimination).

The method may further comprise isolating monocytes from the patient. Monocytes may be isolated from the patient in any suitable manner such as, for example, blood draw or leukaphresis.

The method may further comprise differentiating the monocytes into second dendritic cells. The monocytes may be differentiated into dendritic cells in any suitable manner. For example, the monocytes may be cultured with one or both of granulocyte-macrophage colony-stimulating factor (GM-CSF) and interleukin (IL)-4 until the monocytes exhibit the phenotype of an immature dendritic cell. The time period for developing the phenotype of an immature dendritic cell may vary and may be, e.g., about 72 to about 144 hours. The phenotype of an immature dendritic cell may vary among patients. CD11c is a dendritic cell marker and may be expressed in both immature and mature dendritic cells. CD80, CD86 and CD83 are co-stimulatory molecules expressed by dendritic cells. In most cases, CD80, CD86 and CD83 are highly expressed on mature dendritic cells and moderately expressed on immature dendritic cells. The phenotype of an immature dendritic cell may be characterized, e.g., by the expression of any one or more toll-like receptors (TLR). Alternatively or additionally, the phenotype of an immature dendritic cell may be characterized as being (i) any one or more of CD11c$^+$, CD80$^-$, CD86$^+$, CD83$^+$, CCR7$^-$, and HLA-DR$^+$ or (ii) all of CD11c$^+$, CD80$^-$, CD86$^+$, CD83$^+$, CCR7$^-$, and HLA-DR$^+$.

The method may further comprise inducing the second dendritic cells to present the selected one or more mutated amino acid sequences for which the T cells have antigenic specificity. Other than the one or more mutated amino acid sequences being selected for antigenic specificity, the induction of the second dendritic cells to present the selected one or more mutated amino acid sequences may be as described herein with respect to other aspects of the invention. In an embodiment of the invention, inducing the second dendritic cells to present the selected one or more mutated amino acid sequences may comprise pulsing the second dendritic cells with peptides comprising the selected mutated amino acid sequence or a pool of peptides, each selected peptide in the pool comprising a different selected mutated amino acid sequence or overlapping peptides from the same mutated amino acid sequence, as described herein with respect to other aspects of the invention. In another embodiment of the invention, inducing the second dendritic cells to present the selected one or more mutated amino acid sequences may comprise introducing nucleotide sequence(s) encoding the selected one or more mutated amino acid sequences into the second dendritic cells, as described herein with respect to other aspects of the invention.

Other than being selected for T cell antigenic specificity, the peptides comprising the selected one or more mutated amino acid sequences may be as described herein with respect to other aspects of the invention. In an embodiment of the invention, the peptides comprising the selected one or more mutated amino acid sequences have a length of about 15 to about 40 amino acid residues or about 20 to about 30 amino acid residues. In another embodiment of the invention, the peptides comprising the selected one or more mutated amino acid sequences comprise a minimal T cell epitope, e.g., have a length of about 8 to about 19 amino acid residues. The minimal epitope may be predicted in silico as described herein with respect to other aspects of the invention.

The method further comprises maturing the second dendritic cells. The second dendritic cells may be matured until the second dendritic cells exhibit the phenotype of a mature dendritic cell. The time period for developing the phenotype of a mature dendritic cell may vary and may be, e.g., about 1 to about 12 hours. In an embodiment of the invention, maturing the second dendritic cells comprises maturing the second dendritic cells (i) in the presence of polyinosinic-polycytidylic acid (polyI:C), resiquimod (R848), and interferon (IFN)-gamma and (ii) in the absence of CD40L-expressing K562 cells. In another embodiment of the invention, maturing the second dendritic cells comprises maturing the second dendritic cells (i) in the presence of polyI:C, R848, and IFN-gamma and (ii) in the absence of a further dendritic cell stimulating agent. Further dendritic cell stimulating agents may include, but are not limited to lipopolysaccharide (LPS), CD40L expressing 3T3 cells, IL-1β, IL-6, TNFα, and PGE2. The phenotype of a mature dendritic cell may vary among patients. The phenotype of a mature dendritic cell may be characterized, e.g., by the expression of (i) any one or more of IL-12p70, TNFα, IP-12, MCP-1, MIP-1β, CD80, CD86, CD83, CCR7, and HLA-DR or (ii) all of IL-12p70, TNFα, IP-12, MCP-1, MIP-1β, CD80, CD86, CD83, CCR7, and HLA-DR. Alternatively or additionally, the phenotype of a mature dendritic cell may be characterized, e.g., as being (1) any one or more of CD11c$^+$, CD80$^+$, CD86$^+$, CD83$^{++}$, CCR7$^+$, and HLA-DR$^{++}$ or (2) all of CD11c$^+$, CD80$^+$, CD86$^+$, CD83$^{++}$, CCR7$^+$, and HLA-DR$^{++}$.

The inventive method may produce an isolated population of dendritic cells comprising the matured second dendritic cells which present the selected one or more mutated amino acid sequences for which the T cells have antigenic specificity. The dendritic cells prepared by the inventive methods may be useful for preparing cells for adoptive cell therapies.

Another embodiment of the invention provides an isolated population of dendritic cells prepared according to any of the methods described herein with respect to other aspects of the invention. The population of cells can be a heterogeneous population comprising the dendritic cells which present the selected one or more mutated amino acid sequences for which the T cells have antigenic specificity in addition to at least one other cell, e.g., an antigen presenting cell, which does not present the selected one or more mutated amino acid sequences for which the T cells have antigenic specificity, or a cell other than a dendritic cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of (e.g., consisting essentially of) dendritic cells which present the selected one or more mutated amino acid sequences for which the T cells have antigenic specificity. In an embodiment of the invention, about 1% to about 100%, for example, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100%, or a range defined by any two of the foregoing values, of the population of cells comprises dendritic cells which present the selected one or more mutated amino acid sequences for which the T cells have antigenic specificity.

The inventive populations of dendritic cells can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than about 60%, greater than about 70%, greater than about 80%, greater than about 90% or can be about 100%.

The inventive populations of dendritic cells can be formulated into a composition, such as a pharmaceutical composition. In this regard, the invention provides a pharmaceutical composition comprising any of the inventive populations of dendritic cells and a pharmaceutically acceptable carrier. The inventive pharmaceutical composition can comprise an inventive population of dendritic cells in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive population of cells under consideration. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular inventive population of dendritic cells, as well as by the particular method used to administer the inventive population of dendritic cells. Accordingly, there are a variety of suitable formulations of the pharmaceutical composition of the invention. Suitable formulations may include any of those for oral, parenteral, subcutaneous, intratumoral, intravenous, intramuscular, intraarterial, intrathecal, or interperitoneal administration. More than one route can be used to administer the inventive population of dendritic cells, and in certain instances, a particular route can provide a more immediate and more effective response than another route.

Preferably, the inventive population of dendritic cells is administered by injection, e.g., intravenously. When the inventive population of dendritic cells is to be administered, the pharmaceutically acceptable carrier for the dendritic cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment of the invention, the pharmaceutically acceptable carrier is supplemented with human serum albumin.

In an embodiment of the invention, the pharmaceutical composition may further comprise one or more immune checkpoint inhibitors. Examples of immune checkpoint inhibitors include, but are not limited to, anti-PD-1 antibodies (e.g., pembrolizumab (KEYTRUDA) and nivolumab (OPDIVO)), anti-PD-L1 antibodies, anti-CECAM antibodies, and anti-CTLA-4 antibodies (e.g., ipilimumab (YERVOY)).

In an embodiment of the invention, the pharmaceutical composition may further comprise T cells. Preferably, the T cells have antigenic specificity for the selected one or more mutated amino acid sequences described herein with respect to other aspects of the invention. The T cells may be autologous or allogeneic to the patient. Preferably, the T cells are autologous to the patient. The T cells can include any type of T cell and can be of any developmental stage, as described herein with respect to other aspects of the invention. In an embodiment of the invention, the T cells are TIL.

The T cells in the inventive pharmaceutical composition may comprise a receptor having antigenic specificity for the selected one or more mutated amino acid sequences described herein with respect to other aspects of the invention. The receptor can, for example, be an endogenous TCR, i.e., the TCR that is endogenous or native to (naturally-occurring on) the T cell. In such a case, the T cell comprising the endogenous TCR can be a T cell that was isolated from a mammal which is known to express the antigen. In certain embodiments, the T cell is a primary T cell isolated from a host afflicted with a cancer.

In an embodiment of the invention, the receptor is an exogenous TCR, i.e., an antigen-specific TCR that is not native to (not naturally-occurring on) the T cell. A recombinant TCR is a TCR which has been generated through recombinant expression of one or more exogenous TCR α-, β-, γ-, and/or δ-chain encoding genes. A recombinant TCR can comprise polypeptide chains derived entirely from a single mammalian species, or the antigen-specific TCR can be a chimeric or hybrid TCR comprised of amino acid sequences derived from TCRs from two different mammalian species. For example, the antigen-specific TCR can comprise a variable region derived from a murine TCR, and a constant region of a human TCR such that the TCR is "humanized." Methods of making recombinant TCRs are known in the art. See, for example, U.S. Pat. Nos. 7,820,174; 8,785,601; 8,216,565; and U.S. Patent Application Publication No. 2013/0274203.

In an embodiment of the invention, the T cells in the inventive pharmaceutical composition may comprise a chimeric antigen receptor (CAR) having antigenic specificity for the selected one or more mutated amino acid sequences described herein with respect to other aspects of the invention. Typically, a CAR comprises the antigen binding domain of an antibody, e.g., a single-chain variable fragment (scFv), fused to the transmembrane and intracellular domains of a TCR. Thus, the antigenic specificity of a TCR can be encoded by a scFv which specifically binds to the antigen, or an epitope thereof. Methods of making such chimeric TCRs are known in the art. See, for example, U.S. Pat. No. 8,465,743 and U.S. Patent Application Publication Nos. 2014/0037628 and 2014/0274909.

It is contemplated that the inventive populations of dendritic cells and pharmaceutical compositions can be used in methods of treating or preventing cancer. Without being bound to a particular theory or mechanism, the inventive dendritic are believed to elicit T cells which bind specifically to a mutated amino acid sequence encoded by a cancer-specific mutation, such that TCRs expressed by the elicited T cells are able to mediate an immune response against a target cell expressing the mutated amino acid sequence. In this regard, the invention provides a method of treating or preventing cancer in a patient, comprising administering to the patient any of the pharmaceutical compositions or populations of dendritic cells described herein, in an amount effective to treat or prevent cancer in the patient.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a patient. Furthermore, the treatment or prevention provided by the inventive method can include treatment or prevention of one or more conditions or symptoms of the cancer being treated or prevented. For example, treatment or prevention can include promoting the regression of a tumor. Also, for purposes herein, "prevention" can encompass preventing the recurrence of a cancer or delaying the onset of the cancer, or a symptom or condition thereof.

For purposes of the invention, the amount or dose of the inventive population of dendritic cells or pharmaceutical composition administered (e.g., numbers of dendritic cells when the inventive population of dendritic cells is administered) should be sufficient to effect, e.g., a therapeutic or prophylactic response, in the patient over a reasonable time frame. For example, the dose of the inventive population of dendritic cells or pharmaceutical composition should be sufficient to elicit T cells which bind to a mutated amino acid sequence encoded by a cancer-specific mutation, or treat or prevent cancer in a period of from about 2 hours or longer, e.g., 12 to 24 or more hours, from the time of administration. In certain embodiments, the time period could be even longer. The dose will be determined by the efficacy of the particular inventive population of dendritic cells or pharmaceutical composition administered and the condition of the patient, as well as the body weight of the patient to be treated.

Many assays for determining an administered dose are known in the art. For purposes of the invention, an assay, which comprises comparing the extent to which target cells are lysed or IFN-γ is secreted by T cells upon administration of a given dose of such dendritic cells to a mammal among a set of mammals of which is each given a different dose of the dendritic cells, could be used to determine a starting dose to be administered to a patient. The extent to which target cells are lysed or IFN-γ is secreted upon administration of a certain dose can be assayed by methods known in the art.

The dose of the inventive population of dendritic cells or pharmaceutical composition also will be determined by the existence, nature and extent of any adverse side effects that might accompany the administration of a particular inventive population of dendritic cells or pharmaceutical composition. Typically, the attending physician will decide the dosage of the inventive population of dendritic cells or pharmaceutical composition with which to treat each individual patient, taking into consideration a variety of factors, such as age, body weight, general health, diet, sex, inventive population of dendritic cells or pharmaceutical composition to be administered, route of administration, and the severity of the condition being treated.

In an embodiment in which the inventive population of dendritic cells is to be administered, the number of dendritic cells administered per infusion may vary, for example, in the range of one million to 1 billion cells; however, amounts below or above this exemplary range are within the scope of the invention. For example, the daily dose of inventive host cells can be about 1 million cells, about 5 million cells, about 20 million cells, about 25 million cells, about 30 million cells, about 40 million cells, about 60 million cells, about 70 million cells, about 80 million cells, about 90 million cells, about 120 million cells, about 250 million cells, about 350 million cells, about 450 million cells, about 500 million cells, about 650 million cells, about 800 million cells, about 900 million cells, about 1 billion cells, or a range defined by any two of the foregoing values.

For purposes of the inventive methods, wherein populations of dendritic cells are administered, the dendritic cells can be dendritic cells that are allogeneic or autologous to the patient. Preferably, the dendritic cells are autologous to the patient.

In an embodiment of the invention, the method further comprises administering T cells to the patient. The T cells may be as described herein with respect to other aspects of the invention. The T cells and the inventive dendritic cells may be administered in any sequence. For example, the method may comprise administering the T cells before administering the inventive dendritic cells, after administering the inventive dendritic cells, or simultaneously with the inventive dendritic cells. Alternatively or additionally, the method may comprise administering the inventive dendritic cells before administering the T cells, after administering the T cells, or simultaneously with the T cells. For example, the method may comprise administering first a combination of T cells and the inventive dendritic cells followed by administering further additional inventive dendritic cells e.g., to stimulate the administered T cells in vivo.

Another embodiment of the invention provides any of the isolated population of dendritic cells or pharmaceutical compositions described herein for use in treating or preventing cancer in a patient.

Still another embodiment of the invention provides a set comprising (i) any of the isolated population of dendritic cells or pharmaceutical compositions described herein and (ii) any of the T cells described herein for use in treating or preventing cancer in a patient. The T cells may be as described herein with respect to other aspects of the invention. In an embodiment of the invention, the set further comprises one or more immune checkpoint inhibitors, as described herein with respect to other aspects of the invention.

The cancer may, advantageously, be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the bile duct, cancer of the joints, cancer of the neck, gallbladder, or pleura, cancer of the nose, nasal cavity, or middle ear, cancer of the oral cavity, cancer of the vagina, cancer of the vulva, cholangiocarcinoma, cancer of the endometrium, cancer of the esophagus, chronic lymphocytic leukemia, chronic myeloid cancer, colon cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, urinary bladder cancer, solid tumors, and liquid tumors. The following examples further illustrate the invention but, of course, should not be construed as in any way limiting its scope.

Example 1

This example demonstrates a method of identifying cancer-specific immunogenic epitopes derived from somatic mutations.

Figure 1:
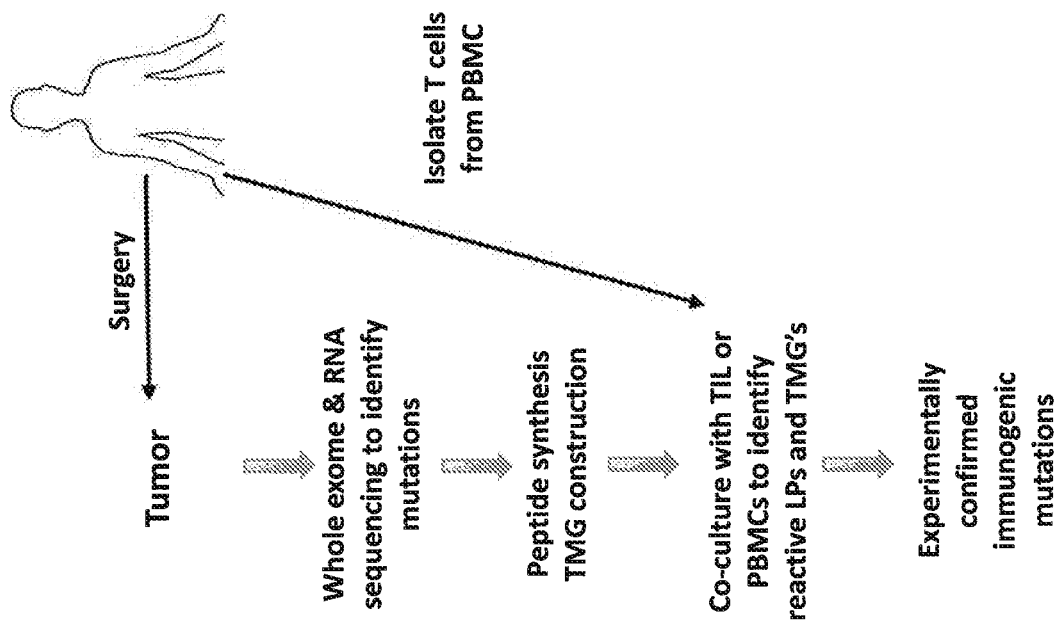
FIG. 1 is a schematic illustrating a method of identifying immunogenic somatic mutations.

A method of identifying immunogenic T cell epitopes derived from neoantigens was developed. A schematic illustrating a method of identifying immunogenic T cell epitopes derived from neoantigens is shown in FIG. 1. The method comprises: (i) whole exome and RNA sequencing analysis of the tumor and a matched normal pheresis sample to identify highly expressed somatic mutations; (ii) construction of tandem minigenes (TMG) and synthesis of long peptides (LP) encompassing these mutations; and (iii) in vitro screening assay to identify T cells in patient tumor infiltrating lymphocyte (TIL) and peripheral blood mononuclear cell (PBMC) samples which recognize the mutated epitopes (Gros et al., *Nat. Med.,* 22(4):433-8 (2016)). This method has been used to screen 25 patients with melanoma, and 64 antigenic somatic mutations were identified with no overlapping between patient tumors (Lu et al., *Clin. Cancer Res.,* 20: 3401-10 (2014); Robbins et al., *Nat. Med.,* 19: 747-52 (2013)). A study to identify antigenic mutations from patients with epithelial cancers including those of the gastrointestinal (GI) tract, genitourinary tract and breast identified 57 non-overlapping somatic mutations. In this study, two patients were also identified who developed a T-cell response against mutated KRAS oncogene (Tran et al., *Science,* 350: 1387-90 (2015)). Neoantigen specific T cells can also be isolated from patient PBMC (Gros et al., *Nat. Med.,* 22(4):433-8 (2016)). By using this method, neoantigen-specific lymphocytes were identified in the peripheral blood of three of four melanoma patients. Despite their low frequency in the circulation, it was found that CD8+PD-1+ cell populations had lymphocytes that targeted unique patient-specific neoantigens.

This method provides a noninvasive approach to identifying antigenic neoantigens. So far, this method has identified more than 190 immunogenic epitopes from multiple cancer types including melanoma, ovarian, colorectal, lung and breast cancers (Table 1) (Gros et al., *Nat. Med.*, 22(4): 433-8 (2016); Lu et al., *Clin. Cancer Res.*, 20: 3401-10 (2014); Tran et al., *Science*, 350(80): 1387-90 (2015); Prickett et al., *Cancer Immunol. Res.*, 4: 669-78 (2016); Tran et al., *Science*, 344: 641-5 (2014); Cohen et al., *J. Clin. Invest.*, 125: 3981-91 (2015)). This method can be applied to any cancer type and can be completed in several weeks. This method can ensure that those antigens are not just expressed in the tumor, but also prompt a significant T cell-mediated immune response.

TABLE 1

| Cancer type | No. of mutations recognized by TIL |
|---|---|
| Colorectal | 38 |
| Pancreas | 4 |
| Bile Duct | 11 |
| Ovary | 7 |
| Endometrium | 2 |
| Lung | 26 |
| Bladder | 3 |
| Esophagus | 12 |
| Breast | 14 |
| Melanoma | 76 |

Example 2

This example demonstrates that DCs matured with PolyI:C, R848, and IFNγ upregulate co-stimulatory molecules and secrete pro-inflammatory cytokines.

It was sought to develop a personalized vaccine (e.g., neoantigen vaccine) which may provide any one or more of (i) an immune response against a variable number of epitopes; (ii) both CD4 and CD8 epitopes; (iii) a cell-mediated Th1 response; and (iv) a method of vaccine manufacture which is less expensive and less time-consuming. To this end, it was sought to develop a vaccine using ex vivo-generated dendritic cells (DCs) from PBMC. DC may be used as antigen presenting cells in the high throughput screening for TIL and PBMC recognition of antigens (e.g., neoantigens). Using the same cells to deliver the vaccine may facilitate the proper processing of antigens and the presentation of the antigens to T cells upon vaccination.

DCs are one of the most effective antigen-presenting cells to induce T cell immunity. Even though immature DCs (iDCs) can uptake, process, and present antigens, they fail to secrete proinflammatory cytokines, and therefore have been shown to be tolerogenic, or at best weakly immunogenic (Steinman, *Annu. Rev. Immunol.*, 30: 1-22 (2012)). Previous studies used multiple maturation cocktails to obtain fully mature DCs. For example, previous studies have used immature DCs or cells activated by a cytokine cocktail (Il-1β, IL-6, TNFα and PGE2) to obtain fully mature DCs.

To evaluate which maturation method is best to get IL-12p70/TNFα-secreting DCs, Day 6 monocyte-derived DCs were incubated with lipopolysaccharide (LPS), CD40L expressing 3T3 cells, TLR mix (PolyI:C, R848, and IFNγ) and cytokine cocktail (Il-1β, IL-6, TNFα and PGE2). Sixteen hours post incubation, the expression level of costimulatory molecules was measured by flow cytometry. The expression of SSC-A and FSC-A was about the same in the immature DCs as compared to the mature DCs (incubated with the TLR mix). Ninety-eight percent of the immature DCs were positive for both CD11c and HLA-DR expression. Ninety-seven percent of the mature DCs (incubated with the TLR mix) were positive for both CD11c and HLA-DR expression. Further flow cytometry data are shown in Tables 2A and 2B. Values in Tables 2A and 2B indicate the percentage of cells with the indicated phenotype.

TABLE 2A

|  | Immature DCs | Mature DCs (incubated with the TLR mix) |
|---|---|---|
| CD83+/CCR7+ | 10 | 49 |
| CD83−/CCR7− | 46 | 21 |
| CD83+/CCR7− | 42 | 20 |
| CD83−/CCR7+ | 2 | 10 |

TABLE 2B

|  | Immature DCs | Mature DCs (incubated with the TLR mix) |
|---|---|---|
| CD80+/CD86+ | 40 | 96 |
| CD80−/CD86+ | 54 | 3 |

The secretion of multiple cytokines and chemokines was measured by multiplex assay. The results are shown in FIGS. 2A-2C.

Figure 2A:
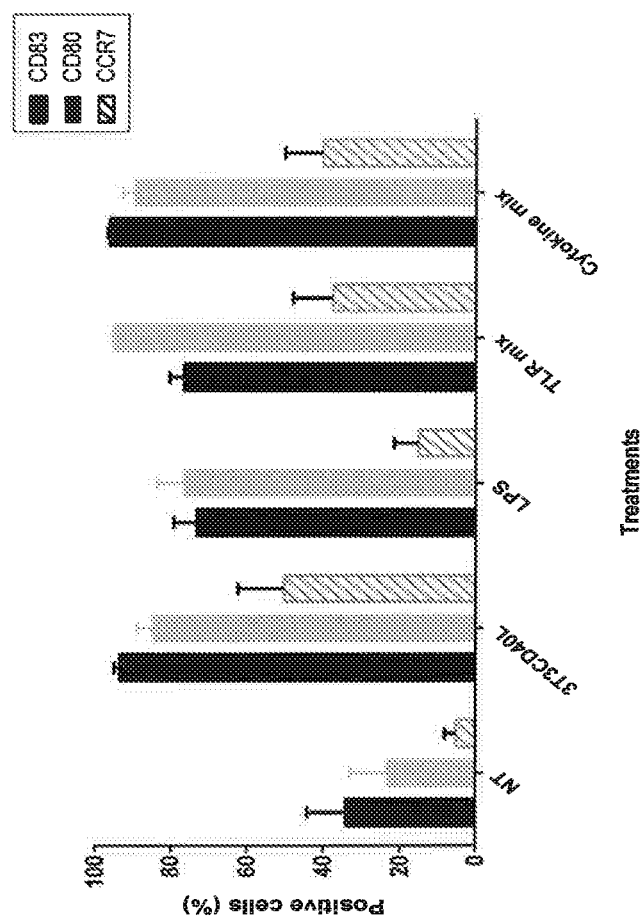
FIG. 2A is a graph showing the percentages of DCs that were positive for the expression of CD83 (black bars), CD80 (grey bars), or CCR7 (hatched bars) following incubation with lipopolysaccharide (LPS), CD40L expressing 3T3 cells, Toll-like receptor (TLR) mix (PolyI:C, R848, and IFNγ) or cytokine mix (Il-1β, IL-6, TNFα, and PGE2). As a negative control, DCs were not treated (NT).
Figure 2C:
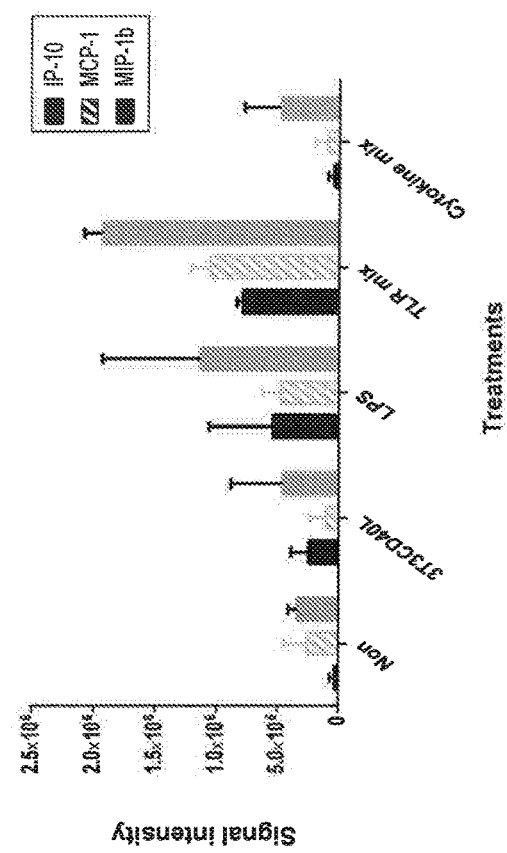
FIG. 2C is a graph showing the signal intensity measured for the secretion of IP-10 (black bars), MCP-1 (hatched bars), or MIP-1b (grey bars) by DCs following incubation with LPS, CD40L expressing 3T3 cells, TLR mix (PolyI:C, R848, and IFNγ) or cytokine mix (Il-1β, IL-6, TNFα, and PGE2). As a negative control, DCs were not treated (non).
Figure 2B:
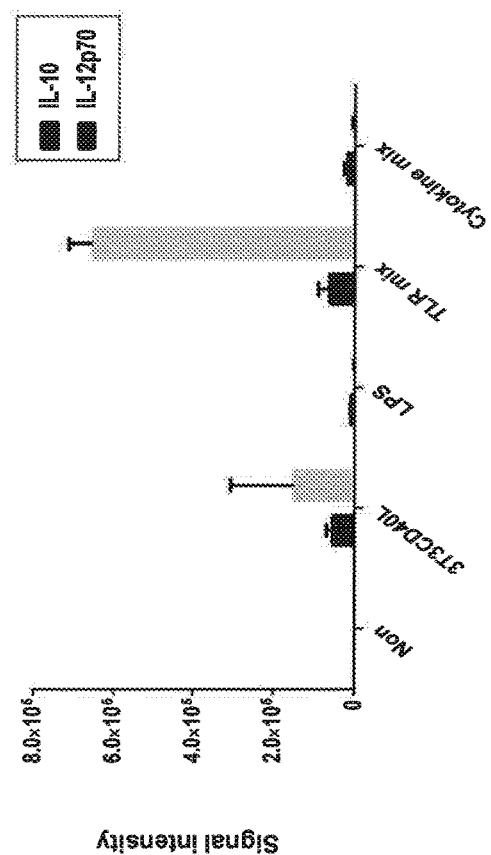
FIG. 2B is a graph showing the signal intensity measured for the secretion of IL-10 (black bars) or IL12p70 (grey bars) by DCs following incubation with LPS, CD40L expressing 3T3 cells, TLR mix (PolyI:C, R848, and IFNγ) or cytokine mix (Il-1β, IL-6, TNFα, and PGE2). As a negative control, DCs were not treated (non).

As shown in Tables 2A and 2B and FIGS. 2A-2C, the TLR mix induced the secretion of IL-12p70, TNFα, IP-12, MCP-1 and MIP-1β. The TLR mix is capable of maturing DCs to secrete Th1 polarizing cytokines and multiple chemokines.

A previous study used a combination of K562-CD40L cells with PolyI:C, R848, and IFNγ to mature monocyte-derived DCs (Carreno et al., *Science*, 348(80): 803-8 (2015)). To evaluate whether the addition of K562-CD40L cells to the TLR mix can induce superior DC maturation, clinical grade K562-CD40L cells (K602C14) were produced and their contribution to DC stimulation was evaluated. As a positive control, the original cells used in the previous study (Carreno et al., *Science*, 348(80): 803-8 (2015)) (K463H) were used. DCs were cultured alone or with (i) K562 cells; (ii) TLR mix; (iii) K463H and TLR mix; or (iv) K602C14 and TLR mix. The expression of CCR7 and CD83 was measured by flow cytometry. The results are shown in Table 3. The values in Table 3 indicate the percentages of cells with the indicated phenotype.

TABLE 3

|  | CD83+/ CCR7+ | CD83−/ CCR7− | CD83+/ CCR7− | CD83−/ CCR7+ |
|---|---|---|---|---|
| DCs cultured alone | 5.32 | 34.5 | 60.0 | 0.22 |
| with K562 cells | 9.11 | 33.9 | 55.5 | 1.51 |
| with TLR mix | 42.7 | 16.3 | 37.5 | 3.43 |
| with K463H and TLR mix | 30.1 | 30.0 | 35.5 | 4.33 |
| with K602C14 and TLR mix | 50.1 | 14.2 | 31.2 | 4.49 |

The secretion of IL-12p70, IL-1b, IL-10, and TNF-α was also measured. The results are shown in FIG. 3.

Figure 3:
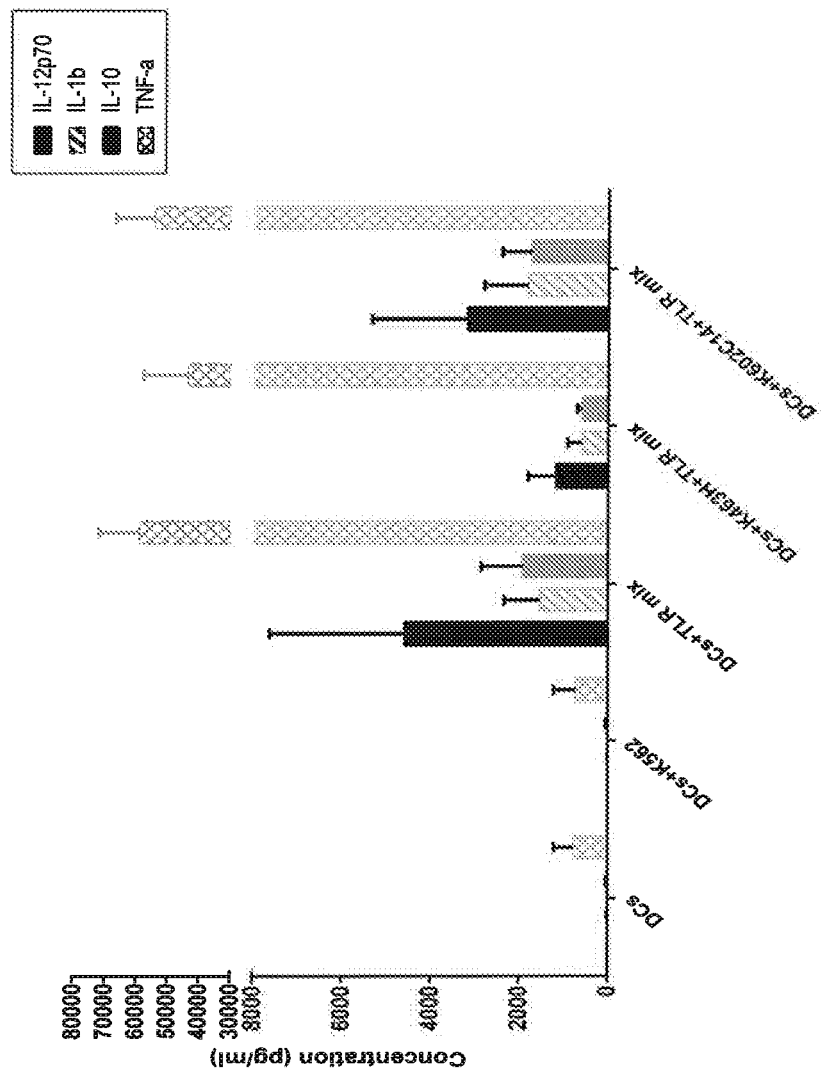
FIG. 3 is a graph showing the concentration (pg/ml) of IL-12p70, IL-1b, IL-10, or TNF-α secreted by DCs cultured alone or with (i) K562 cells; (ii) TLR mix; (iii) K463H and TLR mix; or (iv) K602C14 and TLR mix.

As shown in Table 3 and FIG. 3, the TLR mix alone is sufficient to obtain fully mature DCs. No additional stimulation is needed.

Example 3

This example demonstrates that DCs loaded with long peptides and minimal epitopes stimulate both CD4 and CD8 T cells.

To evaluate the loading method of DCs with antigenic determinants, tandem minigene (TMG) mRNA electroporation of DCs was compared to the loading of the DCs with long peptides and minimal epitopes. A screening system was developed to evaluate the presentation of three CD8 epitopes and three CD4 epitopes in one assay. For that purpose, a series of TMG constructs harboring different signal peptides and targeting signals were made. Long peptides and minimal epitopes encompassing all antigenic determinants were also made (FIG. 4 and Tables 4 and 5). Table 4 shows the minimal epitopes and corresponding long peptides. Table 5 summarizes all of the constructs prepared.

To test antigen presentation, DCs were transfected with one of the TMG constructs, loaded with one of the long peptides, or loaded with one of the minimal epitopes shown in FIGS. 5A and 5B. DCs were co-cultured with PBMC transduced with a TCR recognizing the corresponding antigen, and antigen recognition was evaluated by flow cytometry for 4-1BB expression. The results are shown in FIGS. 5A and 5B.

As shown in FIGS. 5A and 5B, while long peptides and minimal epitopes were recognized by CD4 and CD8 cells, TMGs elicited only CD8 responses. Without being bound to a particular theory or mechanism, it is believed that the CD4 epitopes may not be processed because cytosolic proteins may be abrogating the use of the TMGs as an efficient platform for antigen presentation.

To test if mature DCs can efficiently present both CD4 and CD8 epitopes, DCs were loaded with long peptides or minimal epitopes and stimulated for 16 hours using the TLR mix. Mature DCs were washed and co-incubated with TCR-transduced T cells (FIG. 6A). The upregulation of 4-1BB expression was measured. The results are shown in FIG. 6B.

As shown in FIG. 6B, mature DCs efficiently present both minimal and long epitopes for CD4 and CD8 epitopes.

TABLE 4

| Antigen | HLA restriction | Minimal epitope | Minigene (25mer) |
|---|---|---|---|
| MAGE-A3$_{243-258}$ | DP04 | QHFVQENYLEY (SEQ ID NO: 1) | ILGDPKKLLTQHFVQENYLEYRQVP (SEQ ID NO: 2) |
| gp100$_{44-59}$ | DRB1*0401 | WNRQLYPEWTEAQRLD (SEQ ID NO: 3) | LRTKAWNRQLYPEWTEAQRLDCWRG (SEQ ID NO: 4) |
| Tyrosinase$_{450-462}$ | DRB1*0401 | SYLQDSDPDSFQD (SEQ ID NO: 5) | DLGYDYSYLQDSDPDSFQDYIKSYL (SEQ ID NO: 6) |
| ppp1R3B$_{172m}$ | HLA-A1 | YTDFHCQYVK (SEQ ID NO: 7) | MTFDTWKSYTDFHCQYVKDTYAGSD (SEQ ID NO: 8) |
| HPV16E6$_{29-38}$ | HLA-A2 | TIHDIILECV (SEQ ID NO: 9) | QLCTELQTTIHDIILECVYCKQQLL (SEQ ID NO: 10) |
| HPV16E7$_{11-19}$ | HLA-A2 | YMLDLQPET (SEQ ID NO: 11) | GDTPTLHEYMLDLQPETTDLYCYEQ (SEQ ID NO: 12) |

TABLE 5

| Number | Name | No. of minigenes | Signal peptide | Linker | Targeting sequence | Backbone vector |
|---|---|---|---|---|---|---|
| 1 | mL1-L20-DCLAMP | 20 | Mouse LAMP-1 | None | DC-LAMP | PST1 |
| 2 | HLAA2-L20 | 20 | HLAA2 | None | None | PST1 |
| 3 | HLAA2-F20 | 20 | HLAA2 | Furin cleavage site | None | PST1 |
| 4 | HLAA2-L20-DCLAMP | 20 | HLAA2 | None | DC-LAMP | PST1 |
| 5 | HLAA2-F20-DCLAMP | 20 | HLAA2 | Furin cleavage site | DC-LAMP | PST1 |
| 6 | HLADM-L20 | 20 | HLA-DM | None | None | PST1 |
| 7 | HLADM-F20 | 20 | HLA-DM | Furin cleavage site | None | PST1 |
| 8 | HLADM-F20-DCLAMP | 20 | HLA-DM | None | DC-LAMP | PST1 |
| 9 | hLAMP1-L20 | 20 | Human LAMP1 | Furin cleavage site | None | PST1 |
| 10 | hLAMP1-F20 | 20 | Human LAMP1 | None | None | PST1 |
| 11 | hLAMP1-F20-DCLAMP | 20 | Human LAMP1 | Furin cleavage site | DCLAMP | PST1 |

Mature DCs loaded with long peptides or minimal epitopes encompassing both CD8 and CD4 epitopes were selected for further study.

Example 4

This example demonstrates that mature DCs can stimulate both memory, effector, and naïve neoantigen specific T cells.

To test if DCs matured with the TLR mix are capable of stimulating naïve, antigen-experienced and terminally differentiated effector cells, an in vitro stimulation experiment was conducted, as shown in FIG. 7. Apheresis samples from a colorectal cancer patient were thawed and then incubated in a tissue culture flask. Adherent monocytes were differentiated into DCs, loaded with neoantigen peptide pools, and matured using the TLR mix as described in Example 2. Non-adherent cells were collected, and memory, naïve and terminally differentiated effector memory cells ($T_{EMRA}$) were sorted and stimulated with mature peptide-pulsed autologous DCs in vitro. Ten days after the first stimulation, T cells were re-stimulated with DCs loaded with all peptide pools, and sorted based on 4-1BB and OX40 expression to enrich for neoantigen-specific cells. Cells were then tested for neoantigen-specific recognition using single peptides derived from the most reactive peptide pools.

Neoantigen-specific T cells were selected from naïve, antigen-experienced and $T_{EMRA}$ cells (FIGS. 8A-8D). These results showed that peptide-loaded, TLR mix-stimulated DCs are capable of in vitro activation of T cells derived from memory or naïve precursors.

Example 5

This example demonstrates a rationale for selecting defined, tumor suppressor and driver neoantigens to use in a clinical trial.

Previous studies developed preclinical and clinical neoantigen vaccines using epitopes predicted in silico. Although in silico prediction can select for proper antigens, in many cases, there is no evidence that those antigens are processed and presented by the tumor or antigen presenting cells in the tumor microenvironment. In order to overcome these obstacles, patient TIL and PBMC are pre-screened to identify defined mutated antigens recognized by T cells. In so doing, it is believed that it is more likely that those antigens are processed and presented to T cells in the tumor or the tumor's draining lymph nodes. It is believed that, by augmenting T cell responses against defined neoantigens, the chances of developing a significant clinical response are higher.

In addition, there is growing evidence that targeting tumor driver and suppressor genes can result in superior clinical responses. Mutations in these genes are highly common and can be found in many patients. If mutations in KRAS, NRAS, p53, EGFR or PIK3CA are identified by exome and RNA sequencing, peptides covering those epitopes will be synthesized and used in a vaccine composition. Schematics illustrating the election and synthesis of epitopes are shown in FIGS. 9A and 9B.

Example 6

This example demonstrates a method of preparing an isolated population of dendritic cells which satisfy Certificate of Analysis (COA) criteria.

Validation runs were carried out to perform the process of manufacturing the cell product for a neoantigen DC vaccine. The validation runs were carried out under sterile conditions by the same personnel that will be responsible for the DC production during a clinical trial. The data presented here represent three independent experiments carried out with cells from three different patients.

Dendritic cells were matured with maturation reagents IFN-γ, poly (I:C) and R848 according to the standard operating procedure (SOP) (Carreno et al., Science, 348(80): 803-8 (2015)). Briefly, cryopreserved apheresis vials from Patients 1, 2, and 3 were thawed, and cells were resuspended in DC medium. Cells were counted and resuspended at $5 \times 10^6$ cells/ml in DC medium. Cells were seeded into 175 cm$^2$ flasks and incubated for two hours. After two hours, non-adherent cells were removed, and DC medium with IL-4 and granulocyte-macrophage colony-stimulating factor (GMCSF) was added. On day 3, 10 ml of DC medium with IL-4 and GMCSF was added to support DC growth. On day 5, DCs were harvested and frozen at a concentration of $2-4 \times 10^7$ cells/ml. After 3-10 days, DC were thawed and resuspended at $1 \times 10^6$ cells/ml in DC media with GMCSF and IL-4. DC were transferred into low attachment six well plates (3 ml per well) and pulsed with peptides for 20 hours. For maturation, a mix of IFNγ, R848, and PolyI:C was added to each well for 4 hours. Good laboratory practice (GLP) grade GMCSF and IFNγ (Milteny Biotech) were used during the production of DC from Patient 3's PBMC.

DCs were harvested, counted and evaluated by flow cytometry for CD86 and CD11c expression. The results are shown in FIG. 10A. In two of three experiments, cultures were tested for endotoxin and sterility. A table summarizing the overall recovery rates of all three different patients is presented in Table 6.

TABLE 6

|  | Patient 1 | Patient 2 | Patient 3 |
|---|---|---|---|
| No. of DCs frozen ($\times 10^6$) | 30 | 80 | 60.5 |
| No. of DCs after thawing ($\times 10^6$) | 25 | 52.5 | 42.6 |
| No. of DCs after maturation ($\times 10^6$) | 9 | 25.2 | 23.7 |
| Total recovery (%) | 30 | 31.5 | 39.1 |
| Final product viability (%) | 75 | 80 | 82 |
| Endotoxin test | Negative | Negative | Not tested |
| Sterility test | No growth | No growth | Not tested |

To test antigen presentation, DCs from patient 3 (DPB1*04:01 positive) were loaded with a mix of peptides including the DPB1*04:01-restricted MAGE-A3$_{243-358}$, DRB1*04:01 restricted gp100$_{44-59}$, HLA-A2-restricted HPV16E6$_{29-38}$ and the DRB1*04:01-restricted tyrosinase$_{450-462}$ epitopes. DCs were co-cultured with PBMC transduced with a TCR recognizing the corresponding antigens, and antigen recognition was evaluated by flow cytometry for 4-1BB expression. The results are shown in FIG. 11A. As shown in FIG. 11A, PBMCs transduced with the MAGE-A3 specific TCR recognized the DPB1*04:01 restricted MAGEA3$_{243-358}$ as measured by 4-1BB upregulation.

To test if Patient 3's DCs produce bioactive IL-12p70 following maturation with PolyI:C, r848 and IFNγ, the supernatant was collected at three-time points: (i) before peptide loading, (ii) after peptide loading, and (iii) after maturation. The levels of IL-12p70 were measured by ELISA. The results are shown in FIG. 11B. As shown in FIG. 11B, only the mature DC secreted IL-12p70, while peptide-loaded or immature DC failed to do so.

In all three experiments described in this example, DC were produced successfully and reached the COA criteria. In all three experiments, DC CD11c and CD86 expression were above 70%, which meets the COA criteria for cell identity. In two of three experiments, no bacterial growth or endotoxin levels above the COA criteria were observed during DC production, showing that the GLP grade peptides and DCs are sterile and safe for use. As shown in FIGS. 11A and 11B, the produced DCs can efficiently activate antigen-specific T cells and secrete IL-12p70, which is involved in promoting Th1 immune responses.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

The invention claimed is:

1. A method of inducing an immune response against one or more mutated amino acid sequences in a patient, the method comprising:

identifying one or more mutated amino acid sequences, each mutated amino acid sequence being encoded by a gene comprising a cancer-specific mutation;

inducing first dendritic cells from the patient to present the one or more mutated amino acid sequences, wherein inducing the first dendritic cells to present the one or more mutated amino acid sequences comprises loading the first dendritic cells with peptides comprising the mutated amino acid sequence or a pool of peptides, each peptide in the pool comprising a different mutated amino acid sequence;

co-culturing T cells from the patient with the first dendritic cells;

selecting the one or more mutated amino acid sequences for which the T cells have antigenic specificity, wherein the one or more selected mutated amino acid sequences comprise one or more amino acid sequences presented by a major histocompatibility complex (MHC) Class II molecule and one or more amino acid sequences presented by an MHC Class I molecule;

isolating monocytes from the patient;

differentiating the monocytes into second dendritic cells;

inducing the second dendritic cells to present the selected one or more mutated amino acid sequences for which the T cells have antigenic specificity, wherein inducing the second dendritic cells to present the selected one or more mutated amino acid sequences for which the T cells have antigenic specificity comprises loading the second dendritic cells with peptides comprising the selected mutated amino acid sequence or a pool of peptides, each selected peptide in the pool comprising a different selected mutated amino acid sequence;

maturing the second dendritic cells to provide an isolated population of dendritic cells comprising the matured second dendritic cells which present the selected one or more mutated amino acid sequences for which the T cells have antigenic specificity, wherein CD11c and CD86 expression by the matured second dendritic cells is above 70%; and administering the matured second dendritic cells which present the selected one or more mutated amino acid sequences for which the T cells have antigenic specificity to the patient, whereby an immune response against the one or more mutated amino acid sequences is induced in the patient, wherein maturing the second dendritic cells comprises maturing the second dendritic cells in the presence of polyinosinic-polycytidylic acid (polyI:C), resiquimod (R848), and interferon (IFN)-gamma and in the absence of a further dendritic cell stimulating agent.

2. The method according to claim 1, wherein the peptides loaded into the first dendritic cells and/or the peptides loaded into the second dendritic cells have a length of about 15 to about 40 amino acid residues.

3. The method according to claim 1, wherein the peptides loaded into the first dendritic cells have a length of about 8 to about 19 amino acid residues.

4. The method according to claim 1, wherein the peptides loaded into the second dendritic cells have a length of about 8 to about 19 amino acid residues.

5. The method of claim 1, wherein the T cells which are co-cultured with the first dendritic cells which present the selected one or more mutated amino acid sequences express any one or more of programmed cell death 1 (PD-1), lymphocyte-activation gene 3 (LAG-3), T cell immunoglobulin and mucin domain 3 (TIM-3), 4-1BB, OX40, and CD107a.

6. The method of claim 1, further comprising sequencing the whole exome, the whole genome, or the whole transcriptome of the cancer cell.

7. The method according to claim 1, wherein the matured second dendritic cells express any one or more of IL-12p70, TNFα, IP-12, MCP-1, MIP-1β, CD80, CD86, CD83, CCR7, and HLA-DR.

8. The method according to claim 1, wherein the matured second dendritic cells express all of IL-12p70, TNFα, IP-12, MCP-1, MIP-1β, CD80, CD86, CD83, CCR7, and HLA-DR.

* * * * *

SEQUENCE LISTING

```
<160> NUMBER OF SEQ ID NOS: 12

<210> SEQ ID NO 1
<211> LENGTH: 11
<212> TYPE: PRT
<213> ORGANISM: Artificial Sequence
<220> FEATURE:
<223> OTHER INFORMATION: Synthetic

<400> SEQUENCE: 1

Gln His Phe Val Gln Glu Asn Tyr Leu Glu Tyr
1               5                   10

<210> SEQ ID NO 2
<211> LENGTH: 25
<212> TYPE: PRT
<213> ORGANISM: Artificial Sequence
<220> FEATURE:
<223> OTHER INFORMATION: Synthetic

<400> SEQUENCE: 2

Ile Leu Gly Asp Pro Lys Lys Leu Leu Thr Gln His Phe Val Gln Glu
1               5                   10                  15

Asn Tyr Leu Glu Tyr Arg Gln Val Pro
            20                  25

<210> SEQ ID NO 3
<211> LENGTH: 16
<212> TYPE: PRT
<213> ORGANISM: Artificial Sequence
<220> FEATURE:
<223> OTHER INFORMATION: Synthetic

<400> SEQUENCE: 3

Trp Asn Arg Gln Leu Tyr Pro Glu Trp Thr Glu Ala Gln Arg Leu Asp
```

<210> SEQ ID NO 4
<211> LENGTH: 25
<212> TYPE: PRT
<213> ORGANISM: Artificial Sequence
<220> FEATURE:
<223> OTHER INFORMATION: Synthetic

<400> SEQUENCE: 4

Leu Arg Thr Lys Ala Trp Asn Arg Gln Leu Tyr Pro Glu Trp Thr Glu
1               5                   10                  15

Ala Gln Arg Leu Asp Cys Trp Arg Gly
            20                  25

<210> SEQ ID NO 5
<211> LENGTH: 13
<212> TYPE: PRT
<213> ORGANISM: Artificial Sequence
<220> FEATURE:
<223> OTHER INFORMATION: Synthetic

<400> SEQUENCE: 5

Ser Tyr Leu Gln Asp Ser Asp Pro Asp Ser Phe Gln Asp
1               5                   10

<210> SEQ ID NO 6
<211> LENGTH: 25
<212> TYPE: PRT
<213> ORGANISM: Artificial Sequence
<220> FEATURE:
<223> OTHER INFORMATION: Synthetic

<400> SEQUENCE: 6

Asp Leu Gly Tyr Asp Tyr Ser Tyr Leu Gln Asp Ser Asp Pro Asp Ser
1               5                   10                  15

Phe Gln Asp Tyr Ile Lys Ser Tyr Leu
            20                  25

<210> SEQ ID NO 7
<211> LENGTH: 10
<212> TYPE: PRT
<213> ORGANISM: Artificial Sequence
<220> FEATURE:
<223> OTHER INFORMATION: Synthetic

<400> SEQUENCE: 7

Tyr Thr Asp Phe His Cys Gln Tyr Val Lys
1               5                   10

<210> SEQ ID NO 8
<211> LENGTH: 25
<212> TYPE: PRT
<213> ORGANISM: Artificial Sequence
<220> FEATURE:
<223> OTHER INFORMATION: Synthetic

<400> SEQUENCE: 8

Met Thr Phe Asp Thr Trp Lys Ser Tyr Thr Asp Phe His Cys Gln Tyr
1               5                   10                  15

Val Lys Asp Thr Tyr Ala Gly Ser Asp
            20                  25

<210> SEQ ID NO 9
<211> LENGTH: 10

```
<212> TYPE: PRT
<213> ORGANISM: Artificial Sequence
<220> FEATURE:
<223> OTHER INFORMATION: Synthetic

<400> SEQUENCE: 9

Thr Ile His Asp Ile Ile Leu Glu Cys Val
1               5                   10

<210> SEQ ID NO 10
<211> LENGTH: 25
<212> TYPE: PRT
<213> ORGANISM: Artificial Sequence
<220> FEATURE:
<223> OTHER INFORMATION: Synthetic

<400> SEQUENCE: 10

Gln Leu Cys Thr Glu Leu Gln Thr Thr Ile His Asp Ile Ile Leu Glu
1               5                   10                  15

Cys Val Tyr Cys Lys Gln Gln Leu Leu
            20                  25

<210> SEQ ID NO 11
<211> LENGTH: 9
<212> TYPE: PRT
<213> ORGANISM: Artificial Sequence
<220> FEATURE:
<223> OTHER INFORMATION: Synthetic

<400> SEQUENCE: 11

Tyr Met Leu Asp Leu Gln Pro Glu Thr
1               5

<210> SEQ ID NO 12
<211> LENGTH: 25
<212> TYPE: PRT
<213> ORGANISM: Artificial Sequence
<220> FEATURE:
<223> OTHER INFORMATION: Synthetic

<400> SEQUENCE: 12

Gly Asp Thr Pro Thr Leu His Glu Tyr Met Leu Asp Leu Gln Pro Glu
1               5                   10                  15

Thr Thr Asp Leu Tyr Cys Tyr Glu Gln
            20                  25
```